US008956990B2

(12) United States Patent
Masel et al.

(10) Patent No.: US 8,956,990 B2
(45) Date of Patent: *Feb. 17, 2015

(54) CATALYST MIXTURES

(71) Applicant: Dioxide Materials, Inc., Champaign, IL (US)

(72) Inventors: Richard I. Masel, Champaign, IL (US); Brian Rosen, Champaign, IL (US)

(73) Assignee: Dioxide Materials, Inc., Champaign, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/626,873

(22) Filed: Sep. 25, 2012

(65) Prior Publication Data

US 2013/0023404 A1    Jan. 24, 2013

Related U.S. Application Data

(63) Continuation of application No. PCT/US2011/030098, filed on Mar. 25, 2011.

(51) Int. Cl.
*B01J 31/00* (2006.01)
*B01J 37/34* (2006.01)
(Continued)

(52) U.S. Cl.
CPC *B01J 19/08* (2013.01); *B01J 31/02* (2013.01); *C01B 31/18* (2013.01); *C07C 45/00* (2013.01); *H01M 4/90* (2013.01); *C25B 3/04* (2013.01); *H01M 8/00* (2013.01); *Y02E 60/50* (2013.01)
USPC ............... 502/155; 502/5; 502/162; 502/167; 502/168; 429/416; 429/422

(58) Field of Classification Search
USPC .............. 502/5, 155, 162, 167, 168; 429/416, 429/422
See application file for complete search history.

(56) References Cited

U.S. PATENT DOCUMENTS

| 1,919,850 A | 7/1933 | Luscher |
| 2,511,198 A | 6/1950 | Engel |

(Continued)

FOREIGN PATENT DOCUMENTS

| CA | 1272180 A | 7/1990 |
| CA | 2821642 A1 | 6/2012 |

(Continued)

OTHER PUBLICATIONS

Saeki, T. et al., "Electrochemical reduction of CO2 with high current density in a CO2+methanol medium at various metal electrodes", Journal of Electroanalytical Chemistry 404 (1996), pp. 299-302.

(Continued)

*Primary Examiner* — Patricia L Hailey
(74) *Attorney, Agent, or Firm* — Corridor Law Group, P.C.

(57) ABSTRACT

Catalyst mixtures include at least one Catalytically Active Element and, as a separate constituent, one Helper Catalyst. The catalysts can be used to increase the rate, modify the selectivity or lower the overpotential of chemical reactions. These catalysts are useful for a variety of chemical reactions including, in particular, the electrochemical conversion of $CO_2$. Chemical processes employing these catalysts produce CO, $OH^-$, $HCO^-$, $H_2CO$, $(HCO_2)^-$, $H_2CO_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, or $(COO^-)_2$. Devices using the catalysts include, for example, a $CO_2$ sensor.

62 Claims, 17 Drawing Sheets

(51) Int. Cl.

| | |
|---|---|
| H01M 8/06 | (2006.01) |
| B01J 19/08 | (2006.01) |
| B01J 31/02 | (2006.01) |
| C01B 31/18 | (2006.01) |
| C07C 45/00 | (2006.01) |
| H01M 4/90 | (2006.01) |
| C25B 3/04 | (2006.01) |
| H01M 8/00 | (2006.01) |

(56) References Cited

U.S. PATENT DOCUMENTS

| | | | |
|---|---|---|---|
| 2,996,359 | A | 8/1961 | Mossman et al. |
| 3,959,094 | A | 5/1976 | Steinberg |
| 4,207,151 | A | 6/1980 | Franke et al. |
| 4,240,882 | A | 12/1980 | Ang et al. |
| 4,315,753 | A | 2/1982 | Bruckenstein et al. |
| 4,474,652 | A | 10/1984 | Brown et al. |
| 4,523,981 | A | 6/1985 | Ang et al. |
| 4,545,872 | A | 10/1985 | Sammells et al. |
| 4,595,465 | A | 6/1986 | Ang et al. |
| 4,608,132 | A | 8/1986 | Sammells |
| 4,608,133 | A | 8/1986 | Morduchowitz et al. |
| 4,609,440 | A | 9/1986 | Frese et al. |
| 4,609,441 | A | 9/1986 | Frese, Jr. et al. |
| 4,620,906 | A | 11/1986 | Ang |
| 4,668,349 | A | 5/1987 | Cuellar et al. |
| 4,673,473 | A | 6/1987 | Ang et al. |
| 4,756,807 | A | 7/1988 | Meyer et al. |
| 4,771,708 | A | 9/1988 | Douglass, Jr. |
| 4,789,442 | A | 12/1988 | Nakagawa et al. |
| 4,818,353 | A | 4/1989 | Langer et al. |
| 4,879,070 | A | 11/1989 | Kent |
| 4,968,393 | A | 11/1990 | Mazur et al. |
| 5,064,733 | A | 11/1991 | Krist et al. |
| 5,071,526 | A | 12/1991 | Pletcher et al. |
| 5,089,661 | A | 2/1992 | Maspero et al. |
| 5,206,433 | A | 4/1993 | Hohenschutz et al. |
| 5,284,563 | A | 2/1994 | Fujihira et al. |
| 5,294,740 | A | 3/1994 | Kiefer et al. |
| 5,334,759 | A | 8/1994 | Lippert et al. |
| 5,382,332 | A | 1/1995 | Fujihira et al. |
| 5,639,910 | A | 6/1997 | Ikariya et al. |
| 5,709,789 | A | 1/1998 | Shay et al. |
| 5,763,622 | A | 6/1998 | Podszun et al. |
| 5,804,045 | A | 9/1998 | Orillon et al. |
| 5,879,915 | A | 3/1999 | Loubiere et al. |
| 5,928,806 | A | 7/1999 | Olah et al. |
| 5,952,540 | A | 9/1999 | Lee et al. |
| 6,024,855 | A | 2/2000 | Sharifian et al. |
| 6,429,333 | B1 | 8/2002 | Saari et al. |
| 6,660,680 | B1 | 12/2003 | Hampden-Smith et al. |
| 6,706,657 | B2 * | 3/2004 | Commereuc et al. ......... 502/164 |
| 6,713,649 | B1 | 3/2004 | Hladiy et al. |
| 6,841,700 | B2 | 1/2005 | Auer et al. |
| 6,849,764 | B2 | 2/2005 | Gurkaynak et al. |
| 6,867,329 | B2 | 3/2005 | Auer et al. |
| 6,906,222 | B2 | 6/2005 | Slany et al. |
| 6,955,743 | B2 | 10/2005 | Rousu et al. |
| 6,987,134 | B1 | 1/2006 | Gagnon |
| 6,992,212 | B2 | 1/2006 | Zehner et al. |
| 7,081,547 | B2 | 7/2006 | Fujimoto et al. |
| 7,157,404 | B1 | 1/2007 | Jun et al. |
| 7,241,365 | B2 | 7/2007 | Auer et al. |
| 7,253,316 | B2 | 8/2007 | Pastre et al. |
| 7,323,593 | B2 | 1/2008 | Adami et al. |
| 7,351,860 | B2 | 4/2008 | Adami et al. |
| 7,420,088 | B2 | 9/2008 | Karl et al. |
| 7,459,590 | B2 | 12/2008 | Olah et al. |
| 7,479,570 | B2 | 1/2009 | Ogo et al. |
| 7,605,293 | B2 | 10/2009 | Olah et al. |
| 7,608,743 | B2 | 10/2009 | Olah et al. |
| 7,612,233 | B2 | 11/2009 | Hauk et al. |
| 7,618,725 | B2 | 11/2009 | Masel et al. |
| 7,704,369 | B2 | 4/2010 | Olah et al. |
| 8,313,634 | B2 | 11/2012 | Bocarsly et al. |
| 8,592,633 | B2 | 11/2013 | Cole et al. |
| 2004/0031685 | A1 | 2/2004 | Anderson et al. |
| 2006/0096871 | A1 | 5/2006 | Manoukian et al. |
| 2006/0234174 | A1 | 10/2006 | Burrahm et al. |
| 2006/0235091 | A1 | 10/2006 | Olah et al. |
| 2007/0036706 | A1 | 2/2007 | Ogo et al. |
| 2007/0045125 | A1 | 3/2007 | Hartvigsen et al. |
| 2007/0187247 | A1 | 8/2007 | Lackner et al. |
| 2008/0039538 | A1 | 2/2008 | Olah et al. |
| 2008/0103040 | A1 | 5/2008 | Rodriguez et al. |
| 2008/0223727 | A1 | 9/2008 | Oloman et al. |
| 2009/0014336 | A1 | 1/2009 | Olah et al. |
| 2009/0016948 | A1 | 1/2009 | Young |
| 2009/0169452 | A1 | 7/2009 | Constantz et al. |
| 2009/0289211 | A1 | 11/2009 | Fujioka et al. |
| 2010/0132556 | A1 | 6/2010 | Constantz et al. |
| 2010/0133120 | A1 | 6/2010 | Varney et al. |
| 2010/0135865 | A1 | 6/2010 | Constantz et al. |
| 2010/0137457 | A1 | 6/2010 | Kaplan |
| 2010/0187123 | A1 | 7/2010 | Bocarsly et al. |
| 2010/0193370 | A1 | 8/2010 | Olah et al. |
| 2010/0276287 | A1 | 11/2010 | Manoukian et al. |
| 2011/0114501 | A1 | 5/2011 | Teamey et al. |
| 2011/0114502 | A1 | 5/2011 | Cole et al. |
| 2011/0114503 | A1 | 5/2011 | Sivasankar et al. |
| 2011/0114504 | A1 | 5/2011 | Sivasankar et al. |
| 2011/0226632 | A1 | 9/2011 | Cole et al. |
| 2011/0237830 | A1 | 9/2011 | Masel |

FOREIGN PATENT DOCUMENTS

| | | |
|---|---|---|
| DE | 183856 C | 1/1906 |
| EP | 0012215 A | 6/1980 |
| EP | 0293230 A | 11/1988 |
| EP | 0323300 A | 7/1989 |
| GB | 2230782 A | 10/1990 |
| JP | 201217300 | 1/2012 |
| WO | 2008110830 A | 9/2008 |
| WO | 2010007602 A | 1/2010 |
| WO | 2010063626 A | 6/2010 |
| WO | 2011120021 A | 9/2011 |
| WO | 2012006240 A | 1/2012 |
| WO | WO 2012/006240 | 1/2012 |
| WO | 2013006711 | 1/2013 |

OTHER PUBLICATIONS

Saeki, T. et al., "Electrochemical reduction of liquid CO2. Drastic enhancement of current density", Journal of the Electrochemical Society 141 (1994), pp. L130-L132.

Scheijen, F. et al., "The electrooxidation of small organic molecules on platinum nanoparticles supported on gold: Influence of platinum deposition procedure", Journal of Solid State Electrochemistry 12 (2008), pp. 483-495.

Seshadri, G. et al., "A new homogeneous electrocatalyst for the reduction of carbon dioxide to methanol at low overpotential", J. Electroanalytical Chemistry 372 (1994), pp. 145-150.

Silvester, D.S. et al., "Electrochemical reduction of benzoic acid and substituted benzoic acids in some room temperature ionic liquids", The Journal of Physical Chemistry C112 (2008), pp. 12966-12973.

Silvester, D.S. et al., "Electrochemistry in room temperature ionic liquids: A review and some possible applications", Z. Phys. Chem. 220 (2006), pp. 1247-1274.

Singh, P. et al., "Comparison of Oxygen Reduction Reaction at Silver Nanoparticles and Polycrystalline Silver Electrodes in Alkaline Solution", J. Phys. Chem. 116 (2012), pp. 10656-10663.

Smolinka, T. et al., "CO2 reduction on Pt electrocatalysts and its impact on H 2 oxidation in CO2 containing fuel cell feed gas—A combined in situ infrared spectroscopy, mass spectrometry and fuel cell performance study", Electrochimica Acta 50 (2005), pp. 5189-5199.

Smolinski, S. et al., "Effect of surface order on adsorption of sulfate ions on silver electrodes", Journal of Electroanalytical Chemistry 442 (1998), pp. 41-47.

(56) References Cited

OTHER PUBLICATIONS

Sobkowski, J. et al., "Interaction of sulfate ions with monocrystalline silver electrodes", Colloids Surfaces A: Physicochem. Eng. Aspects 134 (1998), pp. 39-45.

Solla-Gullon, J. et al., "CO monolayer oxidation on semi-spherical and preferentially oriented (1 0 0) and (1 1 1) platinum nanoparticles", Electrochemistry Communications 8 (2006), pp. 189-194.

Solla-Gullon, J. et al., "Shape dependent electrocatalysis", Annual Reports on the Progress of Chemistry—Section C 107 (2011), pp. 263-297.

Solla-Gullon, J. et al., "Shape-dependent electrocatalysis: Methanol and formic acid electrooxidation on preferentially oriented Pt nanoparticles", Physical Chemistry Chemical Physics 10 (2008), pp. 3689-3698.

Star, A. et al., "Nanoelectric carbon dioxide sensors", Advanced Materials 16 (2004), pp. 2049-2051.

Subramanian, K. et al., "Electrochemical membrane reactor for the reduction of carbon dioxide to formate", Journal of Applied Electrochemistry 37 (2007), pp. 255-260.

Sun, J. et al., "Hydroxyl-functionalized ionic liquid: a novel efficient catalyst for chemical fixation of CO2 to cyclic carbonate", Tetrahedron Letters 49 (2008), pp. 3588-3591.

Sung, Y.-E. et al., "Structure of chemisorbed sulfur on a Pt(III) electrode", Journal of the American Chemical Society 119 (1997), pp. 194-200.

Takahashi, I. et al., "Electrochemical reduction of CO2 at copper single crystal Cu(S)-[n(111) Ã—(111)] and Cu(S)-[n (110) Ã—(100)] electrodes", Journal of Electroanalytical Chemistry 533 (2002), pp. 135-143.

Tian, N. et al., "Direct electrodeposition of tetrahexahedral Pd nanocrystals with high-index facets and high catalytic activity for ethanol electrooxidation", Journal of the American Chemical Society 132 (2010), pp. 7580-7581.

Tian, N. et al., "Platinum metal catalysts of high-index surfaces: from single-crystal planes to electrochemically shape-controlled nanoparticles", Journal of Physical Chemistry C112 (2008), pp. 19801-19817.

Tian, N. et al., "Synthesis of tetrahexahedral platinum nanocrystals with high-index facets and high electro-oxidation activity", Science 316 (2007), pp. 732-735.

Udupa, K.S. et al., "Electrolytic reduction of carbon dioxide to formic acid", Electrochimica Acta 16 (1971), pp. 1593-1598.

Welton, T., "Room-Temperature Ionic Liquids. Solvents for Synthesis and Catalysis". Chem. Revs., vol. 99, No. 8 (1999), pp. 2071-2083.

Wong, W.L. et al., "A robust ionic liquid as reaction medium and efficient organocatalyst for carbon dioxide fixation", Chem. Sus. Chem. 1 (2008), pp. 67-70.

Written Opinion of the International Searching Authority issued on Sep. 26, 2012, in connection with PCT/US2011/030098.

Xu, X. et al., "Effects of imidazolium salts as cocatalysts on the copolymerization of CO2 with epoxides catalyzed by (salen)CrlllCl complex", Polymer 48 (2007), pp. 3921-3924.

Yan, T. et al., "Adsorption of CO2 on the rutile (110) surface in ionic liquid. A molecular dynamics simulation", J. Phys.Chem. C 113 (2009), pp. 19389-19392.

Yang, H. et al., "Electrochemical activation of carbon dioxide in ionic liquid: synthesis of cyclic carbonates at mild reaction conditions", Chem. Commun. (2002), pp. 274-275.

Yano, H. et al., "Particle-size effect of nanoscale platinum catalysts in oxygen reduction reaction: An electrochemical and 195Pt EC-NMR study", Physical Chemistry Chemical Physics 8, 4932-4939 (2006).

Yano, H. et al., "Selective electrochemical reduction of CO2 to ethylene at a three-phase interface on copper(I) halide-confined Cu-mesh electrodes in acidic solutions of potassium halides", Journal of Electroanalytical Chemistry 565 (2004), pp. 287-293.

Yano, J. et al., "Selective ethylene formation by pulse-mode electrochemical reduction of carbon dioxide using copper and copper-oxide electrodes", Journal of Solid State Electrochemistry 11 (2006), pp. 554-557.

Yano, M. et al., "Effects of additives in zinc alloy powder on suppressing hydrogen evolution", Journal of Power Sources 74 (1998), pp. 129-134.

Yoshizawa-Fujita, M. et al., "A new class of proton-conducting ionic plastic crystals based on organic cations and dihydrogen phosphate", Electrochemistry Communications 9 (2007), pp. 1202-1205.

Yu, D. et al., "Carboxylation of Terminal Alkynes with Carbon Dioxide Catalyzed by Poly(N-Heterocyclic Carbene)—Supported Silver Nanoparticles", Adv. Synth. Catal. 354 (2012), pp. 969-974.

Yuan, D. et al., "Electrochemical activation of carbon dioxide for synthesis of dimethyl carbonate in an ionic liquid", Electrochimica Acta 54 (2009), pp. 2912-2915.

Zhang, L. et al., "Electrochemical activation of CO2 in ionic liquid (BMIMBF4): synthesis of organic carbonates under mild conditions", Green Chemistry 10 (2008), pp. 202-206.

Zhang, S. et al., "Chiral ionic liquids improved the asymmetric cycloaddition of CO2 to epoxides", Green Chem. 11 (2009), pp. 935-938.

Zhang, Z. et al., "Hydrogenation of carbon dioxide is promoted by a task-specific ionic liquid", Angew. Chem. Int. Ed. 47 (2008), pp. 1127-1129.

Zhang, Z. et al., "Hydrogenation of CO2 to formic acid promoted by a diamine-functionalized ionic liquid", Chem. Sus. Chem. 2 (2009), pp. 234-238.

Zhao, G. et al., "Electrochemical reduction of supercritical carbon dioxide in ionic liquid 1-n-butyl-3-methylimidazolium hexafluorophosphate", Journal of Supercritical Fluids 32 (2004), pp. 287-291.

Zhou, W. et al., "Size effects in electronic and catalytic properties of unsupported palladium nanoparticles in electrooxidation of formic acid", Journal of Physical Chemistry B 110 (2006), pp. 13393-13398.

Zhu, A., "Supported cholinechloride/urea as a heterogeneous catalyst for chemical fixation of carbon dioxide to cyclic carbonates", Green Chemistry. vol. 9 (2007), pp. 169-172.

Kaneco, S. et al. "Effect of sodium cation on the electrochemical reduction of CO2 at a copper electrode in methanol", Journal of Solid State Electrochemistry 11 (2007), pp. 490-495.

Kaneco, S. et al., "Carbon dioxide sequestration technology by electrochemical conversion at cadmium electrode in methanol under mild conditions", Photo/Electrochemistry & Photobiology in Environment, Energy and Fuel (2003), pp. 181-189.

Kaneco, S. et al., "Electrochemical reduction of carbon dioxide to ethylene at a copper electrode in methanol using potassium hydroxide and rubidium hydroxide supporting electrolytes", Electrochimica Acta 51 (2006), pp. 3316-3321.

Kaneco, S. et al., "Electrochemical reduction of carbon dioxide to ethylene with high Faradaic efficiency at a Cu electrode in CsOH/methanol", Electrochimica Acta 44 (1999), pp. 4701-4706.

Kaneco, S. et al., "Electrochemical reduction of CO2 in copper particle-suspended methanol", Chemical Engineering Journal 119 (2006), pp. 107-112.

Kaneco, S. et al., "Electrochemical reduction of CO2 to Methane at the Cu electrode in methanol with sodium supporting salts and its comparison with other alkaline salts", Energy & Fuels 20 (2006), pp. 409-414.

Kaneco, S. et al., "Photoelectrochemical reduction of CO2 at p-InP electrode in copper particle-suspended methanol", Chemical Engineering Journal 148 (2009), pp. 57-62.

Kinge, S. et al., "Dependence of CO oxidation on Pt nanoparticle shape: A shape-selective approach to the synthesis of PEMFC catalysts", Applied Organometallic Chemistry 22 (2008), pp. 49-54.

Kinoshita, K., "Particle size effects for oxygen reduction on highly dispersed platinum in acid electrolytes", Journal of the Electrochemical Society 137 (1990), pp. 845-848.

Koleli, F. et al., "Reduction of CO2 under high pressure and high temperature on Pb-granule electrodes in a fixed-bed reactor in aqueous medium", Applied Catalysis A—General 274 (2004), pp. 237-242.

(56) References Cited

OTHER PUBLICATIONS

Koper, M., "Structure sensitivity and nanoscale effects in electrocatalysis", Nanoscale 3 (2011), pp. 2054-2073.
Laitar, D.S. et al., "Efficient homogeneous catalysis in the reduction of CO2 to CO", Journal of the American Chemical Society 127 (2005), pp. 17196-17197.
Lee, C.W. et al., "Studies on suppression of hydrogen evolution reaction for zinc/air fuel cell", Material Science Forums 539-543 (2007), pp. 1427-1430.
Li, H. et al., "Development of a continuous reactor for the electro-reduction of carbon dioxide to formate—Part 1: Process variables", Journal of Applied Electrochemistry 36 (2006), pp. 1105-1115.
Li, H. et al., "Development of a continuous reactor for the electro-reduction of carbon dioxide to formate—Part 2: Scale-up", Journal of Applied Electrochemistry 37 (2007), pp. 1107-1117.
Li, W., "Electrocatalytic Reduction of CO2 to Small Organic Molecule Fuels on Metal Catalysts", Advances In CO2 Conversion and Utilization (2010), pp. 55-76.
Liu, Y. et al., "Observation of surface structural changes of Pt octahedron nanoparticles and its effect in electrocatalysis oxidation of methanol", Catalysis Communications 10 (2009), pp. 1244-1247.
Liu, Z. et al., "General rules for predicting where a catalytic reaction should occur on metal surfaces: A density functional theory study of C-H and C-O bond breaking/making on flat, stepped, and kinked metal surfaces", Journal of the American Chemical Society 125 (2003), pp. 1958-1967.
Lopez-Cudero, A. et al., "CO electrooxidation on carbon supported platinum nanoparticles: Effect of aggregation", Journal of Electroanalytical Chemistry 644 (2010), pp. 117-126.
Lukaszewski, M. et al., "Electrosorption of carbon dioxide on platinum group metals and alloys—a review", Journal of Solid State Electrochemistry 13 (2009), pp. 813-827.
Lukaszewski, M. et al., "Comparative EQCM study on electrooxidation of carbon oxides adsorption products on noble metals and their alloys. Polycrystalline Pd-based systems", Journal of Electroanalytical Chemistry 606 (2007), pp. 117-133.
Magdesieva, T.V. et al., "Lutetium monophthalocyanine and diphthalocyanine complexes and lithium naphthalocyanine as catalysts for electrochemical CO2 reduction", Journal of the Electrochemical Society 150 (2003), pp. E608-E612.
Maillard, F. et al., "Influence of particle agglomeration on the catalytic activity of carbon-supported Pt nanoparticles in CO monolayer oxidation", Physical Chemistry Chemical Physics 7 (2005), pp. 385-393.
Maillard, F. et al., "Size effects on reactivity of Pt nanoparticles in CO monolayer oxidation: The role of surface mobility", Faraday Discussions 125 (2004), pp. 357-377.
Masel, R., "Chemical Kinetics and Catalysis", Wiley (2001), pp. 702-742.
Meiwes-Broer, K., "Work functions of metal clusters", Hyperfine Interactions 89 (1994), pp. 263-269.
Morris, A. et al., "Electrocatalytic carbon dioxide activation: The rate-determining step of pyridinium-catalyzed CO2 reduction", Chem. Sus. Chem, 4 (2011), pp. 191-196.
Narayanan, R. et al., "Catalysis with transition metal nanoparticles in colloidal solution: Nanoparticle shape dependence and stability", Journal of Physical Chemistry B 109 (2005), pp. 12663-12676.
Noda, H. et al., "Electrochemical reduction of carbon dioxide at various metal electrodes in aqueous potassium hydrogen carbonate solution", Bull. Chem. Soc. Japan 63 (1990), pp. 2459-2462.
Ogura, K. et al., "CO2 attraction by specifically adsorbed anions and subsequent accelerated electrochemical reduction", Electrochimica Acta 56 (2010), pp. 381-386.
Ogura, K. et al., "Reduction of CO2 to ethylene at three-phase interface effects of electrode substrate and catalytic coating", Journal of the Electrochemical Society 152 (2005), pp. D213-D219.
Ogura, K. et al., "Selective formation of ethylene from CO2 by catalytic electrolysis at a three-phase interface", Prepr. Pap.—Am. Chem. Soc., Div. Fuel Chem. 49 (2004), pp. 9-10.
Ohya, S. et al., "Electrochemical reduction of CO2 in methanol with aid of CuO and Cu2O", Catalysis Today 148 (2009), pp. 329-334.
Oloman, C. et al., "Electrochemical processing of carbon dioxide", Chem. Sus. Chem. 1 (2008), pp. 385-391.
O'Mahony, A.M. et al., "The electrochemical reduction of hydrogen sulfide on platinum in several room temperature ionic liquids", The Journal of Physical Chemistry C112 (2008), pp. 7725-7730.
Pease, R.N. et al., "The catalytic combination of ethylene and hydrogen in the presence of metallic copper. III. Carbon monoxide as a catalyst poison", J. Am. Chem. Soc. 47 (1925), pp. 1235-1240.
Perez, E.R. et al., "In situ FT-IR and ex situ EPR analysis for the study of the electroreduction of carbon dioxide in N,N-dimethylformamide on a gold interface", Journal of Electroanalytcal Chemistry 578 (2005), pp. 87-94.
Perez, J. et al., "Particle size effect for ethanol electro-oxidation on Pt/C catalysts in half-cell and in a single direct ethanol fuel cell", Journal of Electroanalytical Chemistry 654 (2011), pp. 108-115.
Photinon, K. et al., "Thick-Film carbon dioxide sensor via anodic adsorbate stripping technique and its structural dependence", Sensors 9 (2009), pp. 7203-7216.
Podlovchenko, B.I. et al., "Electroreduction of carbon dioxide on palladium electrodes at potentials higher than the reversible hydrogen potential", Journal of Electroanalytical Chemistry 373 (1994), pp. 185-187.
Popic, J.P. et al., "Reduction of carbon dioxide on ruthenium oxide and modified ruthenium oxide electrodes in 0.5 M NaHCO3", Journal of Electroanalytical Chemistry 421 (1997), pp. 105-110.
Qu, J. P. et al., "Electrochemical reduction of CO2 on RuO2/TiO2 nanotubes composite modified Pt electrode", Electrochimica Acta 50 (2005), pp. 3576-3580.
Raebiger, J.W. et al., "Electrochemical Reduction of CO2 to CO Catalyzed by a Bimetallic Palladium Complex", Organometallics 25 (2006), pp. 3345-3351.
Rakowski, M. et al., "Development of molecular electrocatalysts for CO2 reduction and H2 production/oxidation", Acc. Chem. Res. 42 (2009), pp. 1974-1982.
Ramirez, G. M. et al., "A supramolecular cobalt-porphyrin-modified electrode, toward the electroreduction of CO2", Journal of Coordination Chemistry 57 (2004), pp. 249-255.
Rezaei, B. et al., "Application of ionic liquids as an electrolyte additive on the electrochemical behavior of lead acid battery", Journal of Power Sources 187 (2009), pp. 605-612.
Rezaei, B. et al., "Effects of tetrabutylammonium hydrogen sulfate as an electrolyte additive on the electrochemical behavior of lead acid battery", Journal of Solid State Electrochemistry 12 (2008), pp. 1663-1671.
Rodriguez, P. et al., "Specific surface reactions for identification of platinum surface domains: Surface characterization and electrocatalytic tests", Electrochimica Acta 50 (2005), pp. 4308-4317.
Rosen, B. et al., "Ionic Liquid-Mediated Selective Conversion of CO2 to CO at Low Overpotentials", Science 334 (2011), pp. 643-644.
International Preliminary Report on Patentability issued on Jan. 3, 2013 in connection with International Application No. PCT/US2011/030098.
International Preliminary Report on Patentability issued on Jan. 3, 2013 in connection with International Application No. PCT/US2011/042809.
Kaneco, S. et al., "Electrochemical conversion of carbon dioxide to formic acid on Pb in KOH/methane electrolyte at ambient temperature and pressure", Energy, vol. 23, No. 12 (1998), pp. 1107-1112.
International Search Report and Written Opinion issued on Feb. 15, 2013 in connection with PCT/US2012/043651.
Arenz, M. et al., "The effect of the particle size on the kinetics of CO electrooxidation on high surface area Pt catalysts", Journal of the American Chemical Society 127 (2005), pp. 6819-6829.
Azuma, M. et al., "Electrochemical reduction of carbon dioxide on various metal, electrodes in low-temperature aqueous KHCO3 media", J. Electrochem. Soc. 137 (1990), pp. 1772-1778.
Barrosse-Antle, L. et al., "Reduction of carbon dioxide in 1-butyl-3-methylimidazolium acetate", Chem. Commun. (2009), pp. 3744-3746.

(56) References Cited

OTHER PUBLICATIONS

Begum, A. et al., "Electrocatalysis of CO2 reduction by ruthenium benzothiazole and bithiazole complexes", Electrochemistry Communications 9 (2007), pp. 2525-2528.
Bell, A.T., "Basic Research Needs: Catalysis for Energy", U.S. Department of Energy Report PNNL-17214 (2008), p. 69.
Blizanac, B. et al., "Oxygen Reduction on Silver Low-Index Single-Crystal in Alkaline Solution: Rotating Ring DiskAg (hkl)", J. Phys. Chem. 110 (2006), pp. 4735-4741.
Bregoli, L., "The influence of platinum crystallite size on the electrochemical reduction of oxygen in phosphoric acid", Electrochimica Acta 23 (1978), pp. 489-492.
Cahill, L. et al., "Investigation of proton dynamics and the proton transport pathway in choline dihydrogen phosphate using solid-state NMR", Physical Chemistry Chemical Physics 12 (2010), pp. 5431-5438.
Chandrasekaran, K. et al., "In-situ spectroscopic investigation of adsorbed intermediate radicals in electrochemical reactions: carbon dioxide CO2- on platinum", Surface Science 185 (1987), pp. 495-514.
Chaplin, R. et al., "Effects of process conditions and electrode material on reaction pathways for carbon dioxide electroreduction with particular reference to formate formation", Journal of Applied Electrochemistry 33 (2003), pp. 1107-1123.
Chen, Q. et al., "Role of surface defect sites: From Pt model surfaces to shape-controlled nanoparticles", Chemical Science 3 (2012), pp. 136-147.
Cherstiouk, O. et al., "Model approach to evaluate particle size effects in electrocatalysis: Preparation and properties of Pt nanoparticles supported on GC and HOPG", Electrochimica Acta 48 (2003), pp. 3851-3860.
Cheung, K.C. et al., "Electrocatalytic reduction of carbon dioxide by a polymeric film of rhenium tricarbonyl dipyridylamine", Journal of Organometallic Chemistry 694 (2009), pp. 2842-2845.
Chu, D. et al., "Fixation of CO2 by electrocatalytic reduction and electropolymerization in ionic liquid-H2O solution", Chem. Sus. Chem. 1 (2008), pp. 205-209.
Cole, E. et al., "Using a one-electron shuttle for the multielectron reduction of CO2 to methanol: kinetic, mechanism, and structural insights", J. Am. Chem. Soc. 132 (2010), pp. 11539-11551.
Danly, D., "Development and commercialization of the Monsanto electrochemical adiponitrile process", J. Electrochemical Soc. 131 (1984), pp. 435C-442C.
Davis, Jr., J.H. et al., "Commercially available salts as building blocks for new ionic liquids", ACS Symp. Ser. 856 (2003), pp. 100-107.
Delacourt, C. et al., "Design of an electrochemical cell making syngas (CO+H2-) from CO2 and H2O reduction at room temperature", Journal of the Electrochemical Society 155 (2008), pp. B42-B49.
Delacourt, C. et al., "Mathematical modeling of a cation-exchange membrane containing two cations", Journal of the Electrochemical Society 155 (2008), pp. B1210-B1217.
Derien, S. et al., "Activation of carbon dioxide: nickel-catalyzed electrochemical carboxylation of diynes", J. Organic Chem. vol. 58. No. 9 (1993), pp. 2578-2588.
DeWulf, D.W. et al., "Electrochemical and surface studies of carbon dioxide reduction to methane and ethylene at copper electrodes in aqueous solutions", Journal of the Electrochemical Society 136 (1989), pp. 1686-1691.
DeWulf, D.W. et al., "The electrochemical reduction of CO2 to CH4 and C2H4 at Cu/Nafion electrodes (solid polymer electrolyte structures)", Catalysis Letters 1 (1988), pp. 73-80.
Dietz, H. et al., "Influence of substituted benzaldehydes and their derivatives as inhibitors for hydrogen evolution in lead/acid batteries", Journal of Power Sources 53 (1995), pp. 359-365.
Dube, P. et al., "Influence of adsorption processes on the CO2 electroreduction: An electrochemical mass spectrometry study", Journal of Electroanalytical Chemistry 582 (2005), pp. 230-240.
DuBois, D. in A. Bard, ed., "Encyclopedia of Electrochemistry", 7a, Springer (2006), pp. 202-225.
DuBois, D. et al., "Electrochemical reduction of carbon dioxide catalyzed by [Pd(triphosphine)(solvent)](BF4)2 complexes: synthetic and mechanistic studies", J. Am. Chem. Soc., vol. 113. No. 23 (1991), pp. 8753-8764.
Eggins, B.R. et al., "Improved yields of oxalate, glyoxylate and glycolate from the electrochemical reduction of carbon dioxide in methanol", Journal of Applied Electrochemistry 27 (1997), pp. 706-712.
Eggins, B.R. et al., "Voltammetry of carbon dioxide. Part 1. A general survey of voltammetry at different electrode materials in different solvents", J. Electroanalytical Chem. 148 (1983), pp. 17-24.
Fisher, B. et al., "Electrocatalytic reduction of carbon dioxide by using macrocycles of nickel and cobalt", J. Am. Chem. Soc., vol. 102, No. 24 (1980), pp. 7361-7363.
Franklin, T.C. et al., "The effect of quaternary ammonium salts on the anodic oxidation of ethanol", Surface Technology 24 (1985), pp. 143-155.
Fukuzumi, S.,"Bioinspired Energy Conversion Systems for Hydrogen Production and Storage", Eur. J. Inorg. Chem., vol. 2008. No. 9. (2008), pp. 1351-1362.
Furuya, N. et al., "High performance Ru—Pd catalysts for CO2 reduction at gas-diffusion electrodes", Journal of Electroanalytical Chemistry 431 (1997), pp. 39-41.
Gattrell, M. et al. "A review of the aqueous electrochemical reduction of CO2 to hydrocarbons at copper", Journal of Electroanalytical Chemistry 594 (2006), pp. 1-19.
Gattrell, M. et al., "Electrochemical reduction of CO2 to hydrocarbons to store renewable electrical energy and upgrade biogas", Energy Conversion Management 48 (2007), pp. 1255-1265.
Haerens, K. et al., "Electrochemical decomposition of choline chloride based ionic liquid analogues", Green Chemistry 11 (2009), pp. 1357-1365.
Himeda, Y., "Conversion of CO2 into formate by homogeneously catalyzed hydrogenation in water: tuning catalytic activity and water solubility through the acid-base equilibrium of the ligand", European Journal of Inorganic Chemistry (2007), pp. 3927-3941.
Hori, Y. et al., "Electrochemical evidence of intermediate formation of adsorbed carbon monoxide in cathodic reduction of carbon dioxide at a nickel electrode", Electrochimica Acta 35 (1990), pp. 1777-1780.
Hori, Y. et al., "Electrochemical reduction of carbon dioxide at various series of copper single crystal electrodes", Journal of Molecular Catalysis A: Chemical 199 (2003), pp. 39-47.
Hori, Y., "Electrochemical CO2 reduction on metal electrodes", Modern Aspects of Electrochemistry 42 (2008), pp. 89-189.
Hoshi, N. et al., "Electrochemical reduction of carbon dioxide at a series of platinum single crystal electrodes", Electrochimica Acta 45 (2000), pp. 4263-4270.
Hoshi, N. et al., "Electrochemical reduction of carbon dioxide on kinked stepped surfaces of platinum inside the stereographic triangle", Journal of Electroanalytical Chemistry 540 (2003), pp. 105-110.
Hoshi, N. et al., "Electrochemical reduction of CO2 on single crystal electrodes of Ag(111), Ag(100), and Ag(110)", Journal of Electroanalytical Chemistry 440 (1997), pp. 283-286.
Ikeda, S. et al., "Electrochemical reduction of carbon dioxide using gas diffusion electrodes loaded with fine catalysts", Nanoscience and Nanotechnology (2008), pp. 108-113.
Ikeda, S. et al., "Zinc ion effect on electrochemical reduction of carbon dioxide at zinc electrode in aqueous solutions", Electrochemistry (Tokyo) 67 (1999), pp. 27-33.
Innocent, B. et al., "Electro-reduction of carbon dioxide to formate on lead electrode in aqueous medium", Journal of Applied Electrochemistry 39 (2009), pp. 227-232.
International Search Report and Written Opinion of the International Searching Authority issued on Oct. 31, 2011, in connection with PCT/US2011/042809.
International Search Report issued on Jul. 6, 2011, in connection with PCT/2011/030098.

(56) References Cited

OTHER PUBLICATIONS

Jiang, T. et al., "Solvent-free synthesis of substituted ureas from CO2 and amines with a functional ionic liquid as the catalyst", Green Chem. 10 (2008), pp. 465-469.

Jitaru, M., "Electrochemical carbon dioxide reduction—Fundamental applied topics (Review)", Journal of the University of Chemical Technology and Metallurgy 42 (2007), pp. 333-344.

Kabbabi, A. et al., "Particle size effect for oxygen reduction and methanol oxidation on Pt/C inside a proton exchange membrane", Journal of Electroanalytical Chemistry 373 (1994), pp. 251-254.

S. Ikeda, T. Takagi, and K. Ito, "Selective Formation of Formic Acid, Oxalic Add, and Carbon Monoxide by Electrochemical Reduction of Carbon Dioxide", Bull. Chem. Soc. Japan, vol. 60, pp. 2517-2522 (1987).

M. Aulice Scibioh and B. Viswanathan,"Electrochemical Reduction of Carbon Dioxide: A Status Report", Indian Natn. Sci. Acad., vol. 70, A, No. 3, pp. 407-462 (May 2004).

Third-Party Submissions Under 37 CFR 1.290, submitted on Sep. 17 and 18, 2013, in connection with co-owned U.S. Appl. No. 12/830,338, and Concise Description of Relevance for each of the references cited in the Third Party Submissions.

International Preliminary Report on Patentability issued on Jan. 9, 2014 in connection with International Application PCT/US2012/043651.

D. Dubois, "Electrochemical Reactions of Carbon Dioxide", Encyclopedia of Electrochemistry, pp. 212 (2007).

Zhu et al., "Supported choline chloride/urea as a heterogeneous catalyst for chemical fixation of carbon dioxide to cyclic carbonates" Green Chemistry 9 (2007) pp. 169-172.

Ma, J. et al., "A short review of catalysis for CO2 conversion", Catal. Today 148 (2009), pp. 221-231.

International Search Report and Written Opinion issued on May 16, 2014 in connection with PCT/US2013/061506.

Urey, H. et al., "Some reactions of atomic hydrogen", Journal of the American Chem. Society 51 (1929), pp. 3286-3290.

Weiss, A. et al., "Formose sugars from formaldehyde", Applied Catalysis 1 (1981), pp. 237-246.

Idriss, H. et al., "Two routes to formaldehyde from formic acid on TiO2, (001) surfaces", Surface Science 348 (1996), pp. 39-48.

Kiss, G. et al., "Palladium-catalyzed reppe carbonylation", Chem. Rev. 101 (2001), pp. 3435-3456.

Jessop, P. et al., "Recent advances in the homogeneous hydrogenatoin of carbon dioxide", Coordination Chem. Rev. 248 (2004), pp. 2425-2442.

Gazsi, A. et al., "Decomposition and reforming of formic acid on supported Au catalysts: Production of CO-free H2", Journal of Physical Chem. C 115 (2011), pp. 15459-15466.

Sabatier, P. et al., "Chimie Organique.—Sur la decomposition catalytique de l 'acide formique", Comptes Rendus Hebdomadaires Des Seances De L'Academie Dessciences 152 (2011), pp. 1213-1215.

Deng, J. et al., "Linked strategy for the production of fuels via formose reaction", Scientific Reports 3 (2013), p. 1244.

International Search Report and Written Opinion issued on Jun. 17, 2014 in connection with PCT/US2014/018067.

Chinese Office Action issued on Aug. 5, 2014 in connection with Chinese Application No. 201180023851.2.

\* cited by examiner

CATALYST MIXTURES

CROSS-REFERENCE TO RELATED APPLICATION(S)

This application is a continuation of International Application No. PCT/US2011/030098, having an international filing date of Mar. 25, 2011, entitled "Novel Catalyst Mixtures". The '098 international application claimed priority benefits, in turn, from U.S. Provisional Patent Application Ser. No. 61/317,955 filed on Mar. 26, 2010, and from U.S. Non-Provisional patent application Ser. No. 12/830,338 filed on Jul. 4, 2010. Each of the '772 international application, the '955 provisional application, and the '338 non-provisional application is hereby incorporated by reference herein in its entirety.

FIELD OF THE INVENTION

The field of the invention is catalysis and catalysts. The catalysts of this invention are applicable, for example, to the electrochemical conversion of carbon dioxide into useful products.

BACKGROUND OF THE INVENTION

There is a present need to decrease carbon dioxide ($CO_2$) emissions from industrial facilities. Over the years, a number of electrochemical processes have been suggested for the conversion of $CO_2$ into useful products. Processes for $CO_2$ conversion and the catalysts for them are discussed in U.S. Pat. Nos. 3,959,094, 4,240,882, 4,523,981, 4,545,872, 4,595,465, 4,608,132, 4,608,133, 4,609,440, 4,609,441, 4,609,451, 4,620,906, 4,668,349, 4,673,473, 4,711,708, 4,756,807, 4,818,353, 5,064,733, 5,284,563, 5,382,332, 5,457,079, 5,709,789, 5,928,806, 5,952,540, 6,024,855, 6,660,680, 6,987,134 (the '134 patent), 7,157,404, 7,378,561, 7,479,570, U.S. Pat. App. Pub. No. 2008/0223727 (the '727 application) and papers reviewed by Hori (Modern Aspects of Electrochemistry, 42, 89-189, 2008) ("the Hori Review"), Gattrell, et al. (Journal of Electroanalytical Chemistry, 594, 1-19, 2006) ("the Gattrell review"), DuBois (Encyclopedia of Electrochemistry, 7a, 202-225, 2006) ("the DuBois review"), and the papers Li, et al. (Journal of Applied Electrochemistry, 36, 1 105-1115, 2006, Li, et al. (Journal of Applied Electrochemistry, 37, 1107-1 117, 2007, and Oloman, et al. (ChemSusChem, 1, 385-391, 2008) ("the Li and Oloman papers").

Generally an electrochemical cell contains an anode 50, a cathode 51 and an electrolyte 53, as indicated in FIG. 1. The cell can also include a membrane 52. Catalysts are placed on the anode, and or cathode and or in the electrolyte to promote desired chemical reactions. During operation, reactants or a solution containing reactants is fed into the cell. Then a voltage is applied between the anode and the cathode, to promote an electrochemical reaction.

When an electrochemical cell is used as a $CO_2$ conversion system, a reactant comprising $CO_2$, carbonate or bicarbonate is fed into the cell. A voltage is applied to the cell, and the $CO_2$ reacts to form new chemical compounds. Examples of cathode reactions in the Hori Review include:

$CO_2 + 2e^- \rightarrow CO + O_2$ $2CO_2 + 2e^- \rightarrow CO + CO_3^{2-}$ $CO_2 + H_2O + 2e^- \rightarrow CO + 2OH^-$ $CO_2 + 2H_2O + 4e^- \rightarrow HCO^- + 3OH^-$ $CO_2 + 2H_2O + 2e^- \rightarrow H_2CO + 2OH^-$ $CO_2 + H_2O + 2e^- \rightarrow (HCO_2)^- + OH^-$ $CO_2 + 2H_2O + 2e^- \rightarrow H_2CO_2 + 2OH-$ $CO_2 + 6H_2O + 6e^- \rightarrow CH_3OH + 6OH^-$ $CO_2 + 6H_2O + 8e^- \rightarrow CH_4 + 8OH^-$ $2CO_2 + 8H_2O + 12e^- \rightarrow C_2H_4 + 12OH^-$ $2CO_2 + 9H_2O + 12e^- \rightarrow CH_3CH_2OH + 12OH^-$ $2CO_2 + 6H_2O + 8e^- \rightarrow CH_3COOH + 8OH^-$ $2CO_2 + 5H_2O + 8e^- \rightarrow CH_3COO^- + 7OH^-$ $CO_2 + 10H_2O + 14e^- \rightarrow C_2H_6 + 14OH^-$ $CO_2 + 2H^+ + 2e^- \rightarrow CO + H2O$, acetic acid, oxalic acid, oxylate $CO_2 + 4H^+ + 4e^- \rightarrow CH_4 + O_2$ where e– is an electron. The examples given above are merely illustrative and are not meant to be an exhaustive list of all possible cathode reactions.

Examples of reactions on the anode mentioned in the Hori Review include:

$2O^{2-} \rightarrow O_2 + 4e-$ $2CO_3^{2-} \rightarrow O_2 + 2CO_2 + 4e-$ $4OH^- \rightarrow O_2 + 2H_2O + 4e-$ $2H_2O \rightarrow O_2 + 4H^+ + 4e-$ The examples given above are merely illustrative and are not meant to be an exhaustive list of all possible anode reactions.

In the previous literature, catalysts comprising one or more of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd have all shown activity for $CO_2$ conversion. Reviews include Ma, et al. (Catalysis Today, 148, 221-231, 2009), Hori (Modern Aspects of Electrochemistry, 42, 89-189, 2008), Gattrell, et al. (Journal of Electroanalytical Chemistry, 594, 1-19, 2006), DuBois (Encyclopedia of Electrochemistry, 7a, 202-225, 2006) and references therein.

The results in the Hori Review show that the conversion of $CO_2$ is only mildly affected by solvent unless the solvent also acts as a reactant. Water can act like a reactant, so reactions in water are different than reactions in non-aqueous solutions. But the reactions are the same in most non-aqueous solvents, and importantly, the overpotentials are almost the same in water and in the non-aqueous solvents.

Zhang, et al. (ChemSusChem, 2, 234-238, 2009) and Chu, et al. (ChemSusChem, 1, 205-209, 2008) report $CO_2$ conversion catalyzed by an ionic liquid. Zhao, et al. (The Journal of Supercritical Fluids, 32, 287-291, 2004) and Yuan, et al., (Electrochimica Acta 54 (2009) 2912-2915) report the use of an ionic liquid as a solvent and electrolyte, but not a co-catalyst, for $CO_2$ electroconversion. Each of these papers is incorporated by reference. Catalyst Today Volume 48, pages 189-410 November 2009 provides the proceedings of the 10th international conference on $CO_2$ utilization. These pages are incorporated by reference. The catalysts have been in the form of either bulk materials, supported particles, collections of particles, small metal ions or organometallics. Still, according to Bell (A. Bell. Ed, Basic Research Needs, Catalysis For Energy, US Department Of Energy Report PNNL17712, 2008) ("the Bell Report"), "The major obstacle preventing efficient conversion of carbon dioxide into energy-bearing products is the lack of catalyst" with sufficient activity at low overpotentials and high electron conversion efficiencies.

The overpotential is associated with lost energy of the process, and so one needs the overpotential to be as low as possible. Yet, according to The Bell Report "Electron conversion efficiencies of greater than 50 percent can be obtained, but at the expense of very high overpotentials". This limitation needs to be overcome before practical processes can be obtained.

The '134 patent also considers the use of salt (NaCl) as a secondary "catalyst" for $CO_2$ reduction in the gas phase, but salt does not lower the overpotential for the reaction.

A second disadvantage of many of the catalysts is that they also have low electron conversion efficiency. Electron conversion efficiencies over 50% are needed for practical catalyst systems.

The examples above consider applications for $CO_2$ conversion, but the invention overcomes limitations of other systems. For example some commercial $CO_2$ sensors use an electrochemical reaction to detect the presence of $CO_2$. At present, these sensors require over 1-5 watts of power, which is too high for portable sensing applications.

Finally, the invention considers new methods to form formic acid. Other methods are discussed in U.S. Pat. Nos. 7,618,725, 7,612,233, 7,420,088, 7,351,860, 7,323,593, 7,253,316, 7,241,365, 7,138,545, 6,992,212, 6,963,909, 6,955,743, 6,906,222, 6,867,329, 6,849,764, 6,841,700, 6,713,649, 6,429,333, 5,879,915, 5,869,739, 5,763,662, 5,639,910, 5,334,759, 5,206,433, 4,879,070, and 4,299,891. These processes do not use $CO_2$ as a reactant.

SUMMARY OF THE INVENTION

The invention provides a novel catalyst mixture that can overcome one or more of the limitations of low rates, high overpotentials and low electron conversion efficiencies (namely, selectivities) for catalytic reactions and high power for sensors. The catalyst mixture includes at least one Catalytically Active Element, and at least one Helper Catalyst. When the Catalytically Active Element and the Helper Catalyst are combined, the rate and/or selectivity of a chemical reaction can be enhanced over the rate seen in the absence of the Helper Catalyst. For example, the overpotential for electrochemical conversion of carbon dioxide can be substantially reduced, and the current efficiency (namely, selectivity) for $CO_2$ conversion can be substantially increased.

The invention is not limited to catalysts for $CO_2$ conversion. In particular, catalysts that include Catalytically Active Elements and Helper Catalysts might enhance the rate of a wide variety of chemical reactions. Reaction types include: homogeneously catalyzed reactions, heterogeneously catalyzed reactions, chemical reactions in chemical plants, chemical reactions in power plants, chemical reactions in pollution control equipment and devices, chemical reactions in fuel cells, and chemical reactions in sensors. The invention includes all of these examples. The invention also includes processes using these catalysts.

DETAILED DESCRIPTION OF PREFERRED EMBODIMENT(S)

Figure 1:
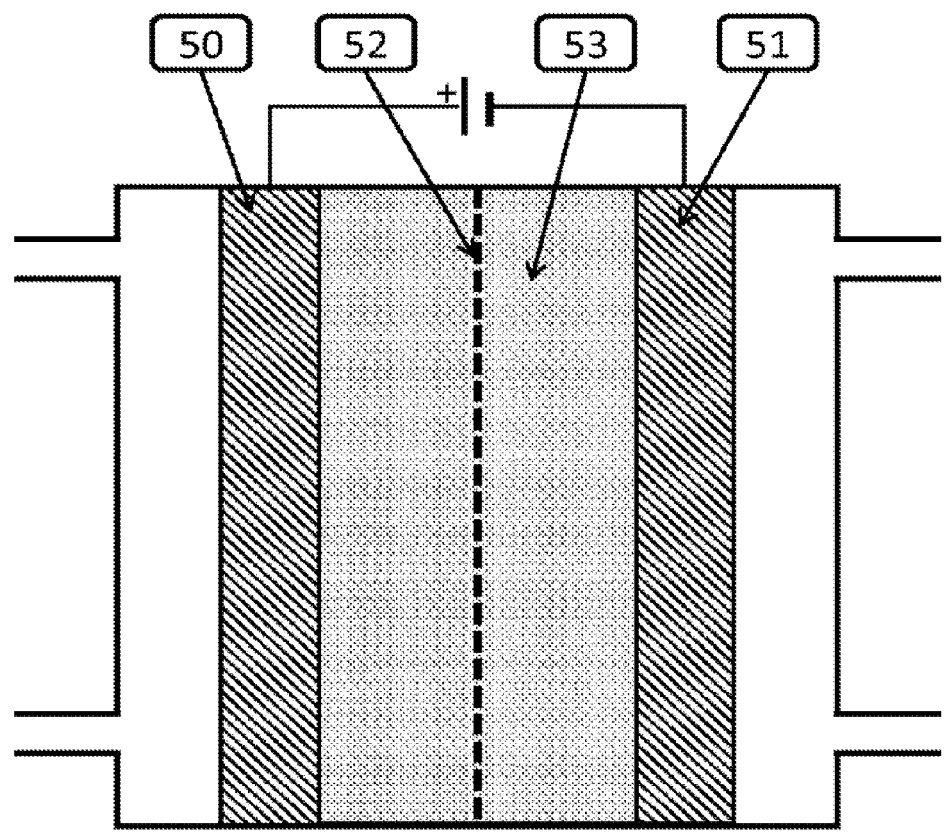
FIG. 1 is a diagram of a typical electrochemical cell.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is to be noted that as used herein and in the appended claims, the singular forms "a," "an," and "the" include the plural reference unless the context clearly dictates otherwise. Thus, for example, a reference to "a linker" is a reference to one or more linkers and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical value ranges recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value are to be treated in a similar manner.

Moreover, provided immediately below is a "Definitions" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

Definitions

The term "electrochemical conversion of $CO_2$" as used here refers to any electrochemical process where carbon dioxide, carbonate, or bicarbonate is converted into another chemical substance in any step of the process.

The term "CV" as used here refers to a cyclic voltamogram or cyclic voltammetry.

The term "Overpotential" as used here refers to the potential (voltage) difference between a reaction's thermodynamically determined reduction or oxidation potential and the potential at which the event is experimentally observed.

The term "Cathode Overpotential" as used here refers to the overpotential on the cathode of an electrochemical cell.

The term "Anode Overpotential" as used here refers to the overpotential on the anode of an electrochemical cell.

The term "Electron Conversion Efficiency" refers to selectivity of an electrochemical reaction. More precisely, it is defined as the fraction of the current that is supplied to the cell that goes to the production of a desired product.

The term "Catalytically Active Element" as used here refers to any chemical element that can serve as a catalyst for the electrochemical conversion of $CO_2$.

The term "Helper Catalyst" refers to any organic molecule or mixture of organic molecules that does at least one of the following:

(a) Speeds up a chemical reaction or (b) Lowers the overpotential of the reaction without being substantially consumed in the process.

The term "Active Element, Helper Catalyst Mixture" refers to any mixture that includes one or more Catalytically Active Element(s) and at least one Helper Catalyst The term "Ionic Liquid" refers to salts or ionic compounds that form stable liquids at temperatures below 200° C.

The term "Deep Eutectic Solvent" refers to an ionic solvent that includes a mixture which forms a eutectic with a melting point lower than that of the individual components.

Specific Description

The invention relates generally to Active Element, Helper Catalyst Mixtures where the mixture does at least one of the following:

Speeds up a chemical reaction, or

Lowers the overpotential of the reaction, without being substantially consumed in the process.

For example such mixtures can lower the overpotential for $CO_2$ conversion to a value less than the overpotentials seen when the same Catalytically Active Element is used without the Helper Catalyst.

According to the Hori Review, Gattrell, et al. (Journal of Electroanalytical Chemistry, 594, 1-19, 2006), DuBois (Encyclopedia of Electrochemistry, 7a, 202-225, 2006) and references therein, catalysts including one or more of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd all show activity for $CO_2$ conversion. Products include one or more of CO, $OH^-$, $HCO^-$, $H_2CO$, $(HCO_2)^-$, $H_2O_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, and $(COO^-)_2$. Therefore, V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd are each examples of Catalytically Active Elements, but the invention is not limited to this list of chemical elements. Possible products of the reaction include one or more of CO, $OH^-$, $HCO^-$, $H_2CO$, $(HCO_2)^-$, $H_2CO_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, and $(COO^-)_2$, but the invention is not limited to this list of products.

The Hori Review also notes that Pb, Hg, Tl, In, Cd, Bi, Zr, Cr, Sn and W are best for formic acid production. Furuya, et al. (Journal of Electroanalytical Chemistry, 431, 39-41, 1997) notes that Pd/Ru is also active.

The Hori Review notes that there has been over 30 years of work on the electrochemical conversion of $CO_2$ into saleable products, but still, according to the Bell Report "Electron conversion efficiencies of greater than 50 percent can be obtained, but at the expense of very high overpotentials". This limitation needs to be overcome before practical processes can be obtained.

Figure 2:
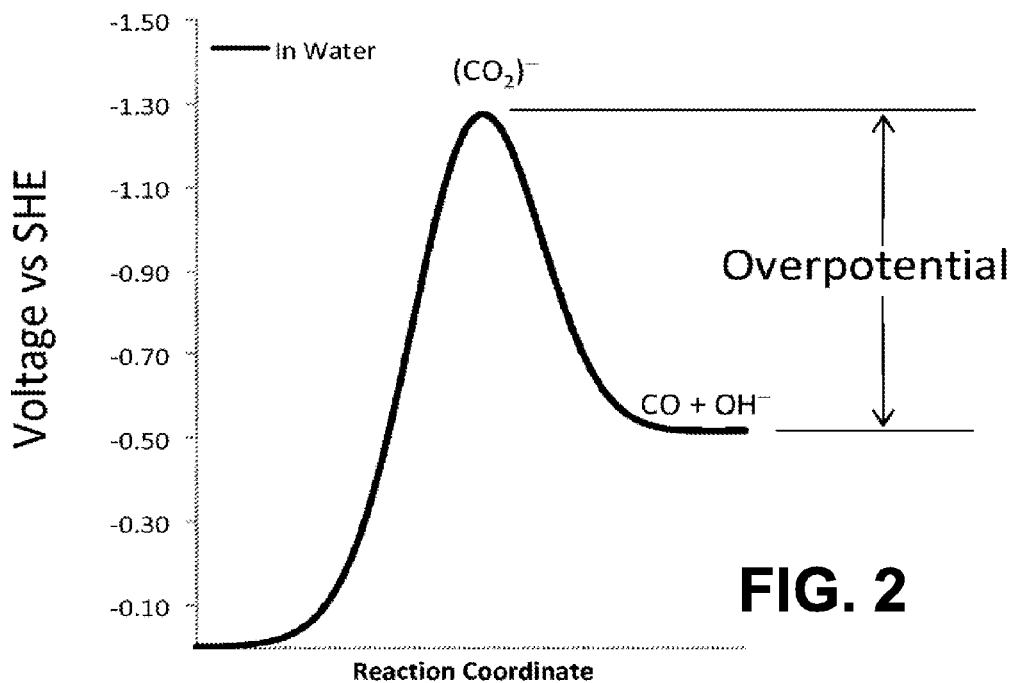
FIG. 2 is a schematic of how the potential of the system moves as it proceeds along the reaction coordinate in the absence of the ionic liquid if the system goes through a $(CO_2)^-$ intermediate. The reaction coordinate indicates the fraction of the reaction that has been completed. A high potential for $(CO_2)^-$ formation can create a high overpotential for the reaction.
Figure 3:
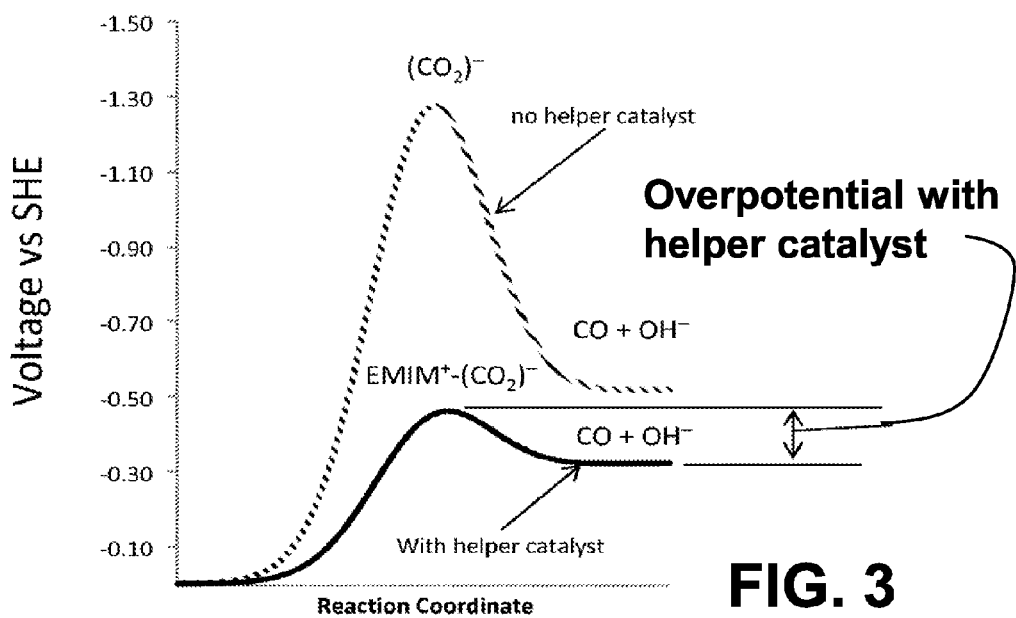
FIG. 3 illustrates how the potential could change when a Helper Catalyst is used. In this case the reaction could go through a $CO_2$-EMIM complex rather than a $(CO_2)^-$, substantially lowering the overpotential for the reaction.

FIGS. 2 and 3 illustrate one possible mechanism by which a Helper Catalyst can enhance the rate of $CO_2$ conversion. According to Chandrasekaran, et al. (Surface Science, 185, 495-514, 1987) the high overpotentials for $CO_2$ conversion occur because the first step in the electroreduction of $CO_2$ is the formation of a $(CO_2)^-$ intermediate. It takes energy to form the intermediate as illustrated in FIG. 2. This results in a high overpotential for the reaction.

FIG. 3 illustrates what might happen if a solution containing 1-ethyl-3-methylimidazolium ($EMIM^+$) cations is added to the mixture. $EMIM^+$ might be able to form a complex with the $(CO_2)^-$ intermediate. In that case, the reaction could proceed via the $EMIM^+$-$(CO_2)^-$ complex instead of going through a bare $(CO_2)^-$ intermediate as illustrated in FIG. 3. If the energy to form the $EMIM^+$-$(CO_2)^-$ complex is less than the energy to form the $(CO_2)^-$ intermediate, the overpotential for $CO_2$ conversion could be substantially reduced. Therefore any substance that includes $EMIM^+$ cations could act as a Helper Catalyst for $CO_2$ conversion.

In most cases, solvents only have small effects on the progress of catalytic reactions. The interaction between a solvent and an adsorbate is usually much weaker than the interaction with a Catalytically Active Element, so the solvent only makes a small perturbation to the chemistry occurring on metal surfaces. However, the diagram in FIG. 3 shows that such an effect could be large.

Of course a Helper Catalyst, alone, will be insufficient to convert $CO_2$. Instead, one still needs a Catalytically Active Element that can catalyze reactions of $(CO_2)^-$ in order to get high rates of $CO_2$ conversion. Catalysts including at least one of the following Catalytically Active Elements have been previously reported to be active for electrochemical conversion of $CO_2$:

V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd.

Many of these catalysts also show activity for a number of other reactions. All of these elements are specifically included as Catalytically Active Elements for the purposes of the invention. This list of elements is meant for illustrative purposes only, and is not meant to limit the scope of the invention.

Further, those skilled in the art should realize that the diagram in FIG. 3 could be drawn for any molecule that could form a complex with $(CO_2)^-$. Previous literature indicates that solutions including one or more of: ionic liquids, deep eutectic solvents, amines, and phosphines; including specifically imidazoliums (also called imidazoniums), pyridiniums, pyrrolidiniums, phosphoniums, ammoniums, sulfoniums, prolinates, and methioninates can form complexes with $CO_2$. Consequently, they may serve as Helper Catalysts. Also Davis Jr., et al. (In ACS Symposium Series 856: Ionic Liquids as Green Solvents: Progress and Prospects, 100-107, 2003) list a number of other salts that show ionic properties. Specific examples include compounds including one or more of acetocholines, alanines, aminoacetonitriles, methylammoniums, arginines, aspartic acids, threonines, chloroformamidiniums, thiouroniums, quinoliniums, pyrrolidinols, serinols, benzamidines, sulfamates, acetates, carbamates, triflates, and cyanides. These salts may act as Helper Catalysts. These examples are meant for illustrative purposes only, and are not meant to limit the scope of the invention.

Of course, not every substance that forms a complex with $(CO_2)^-$ will act as a Helper Catalyst. Masel (Chemical Kinetics and Catalysis, Wiley 2001, p. 717-720) notes that when an intermediate binds to a catalyst, the reactivity of the intermediate decreases. If the intermediate bonds too strongly to the catalyst, the intermediate will become unreactive, so the substance will not be effective. This provides a key limitation on substances that act as Helper Catalysts. The Helper Catalyst cannot form so strong a bond with the $(CO_2)^-$ that the $(CO_2)^-$ is unreactive toward the Catalytically Active Element.

More specifically, one wishes the substance to form a complex with the $(CO_2)^-$ so that the complex is stable (that is, has a negative free energy of formation) at potentials less negative than $-1$ V with respect to the standard hydrogen electrode (SHE.) However, the complex should not be so stable that the free energy of the reaction between the complex and the Catalytically Active Element is more positive than about 3 kcal/mol.

Those trained in the state of the art should realize that the ability of the Helper Catalyst to stabilize the $(CO_2)^-$ also varies with the anion. For example Zhao, et al. (The Journal of Supercritical Fluids, 32, 287-291, 2004) examined $CO_2$ conversion in 1-n-butyl-3-methylimidazolium hexafluorophosphate (BMIM-PF6), but FIG. 3 in Zhao, et al., shows that the BMIM-PF6 did NOT lower the overpotential for the reaction (that is, the BMIM-PF6 did not act as a Helper Catalyst.) This may be because the BMIM-PF6 formed such a strong bond to the $(CO_2)^-$ that the $CO_2$ was unreactive with the copper. Similarly Yuan, et al., Electrochimica Acta 54 (2009) 2912-2915, examined the reaction between methanol and $CO_2$ in 1-butyl-3-methylimidazolium bromide (BMIM-Br). The BMIM-Br did not act as a Helper Catalyst. This may be because the complex was too weak or that the bromine poisoned the reaction.

Figure 4A:
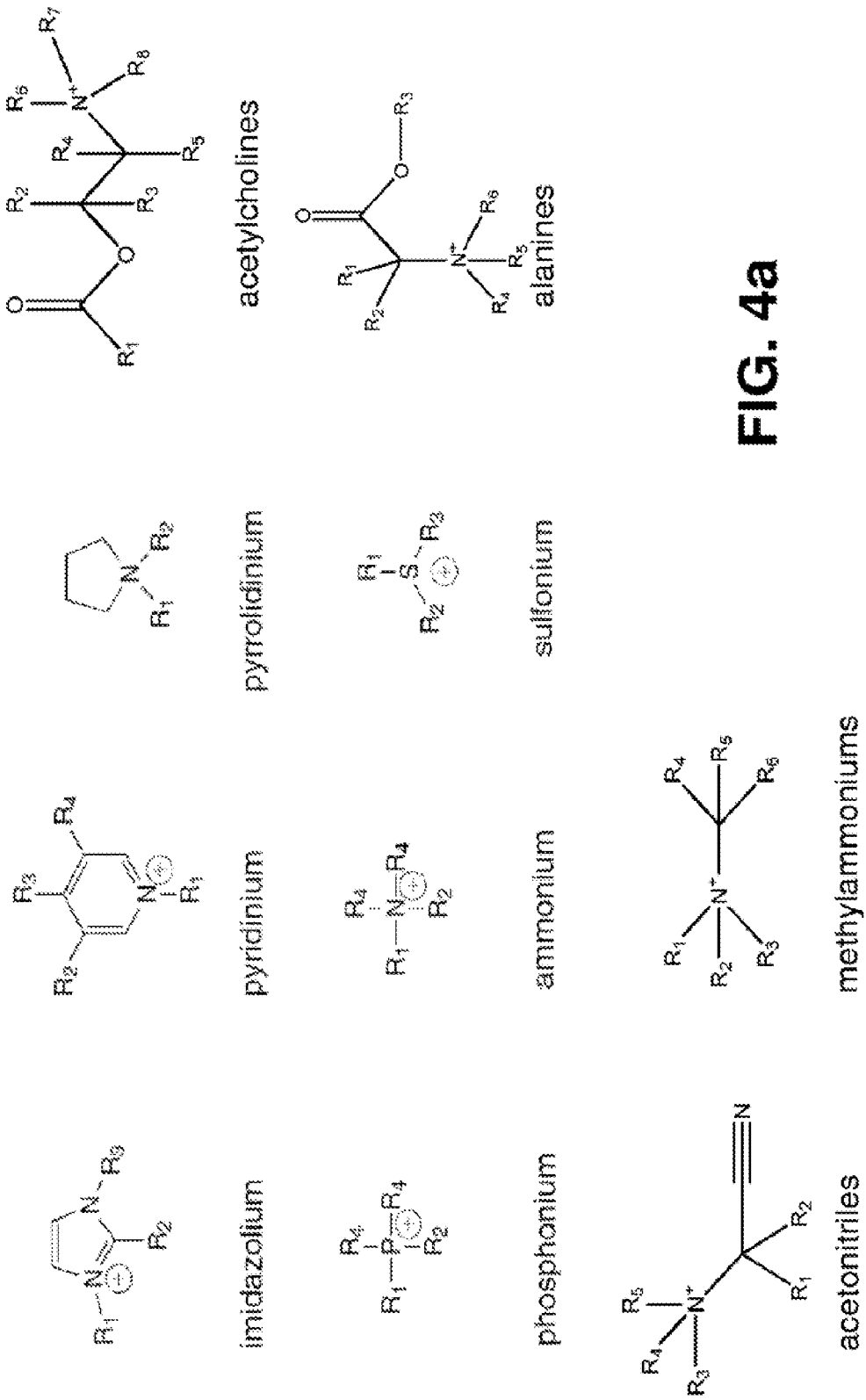
FIGS. 4a, 4b and 4c illustrate some of the cations that may be used to form a complex with $(CO_2)^-$.
Figure 4B:
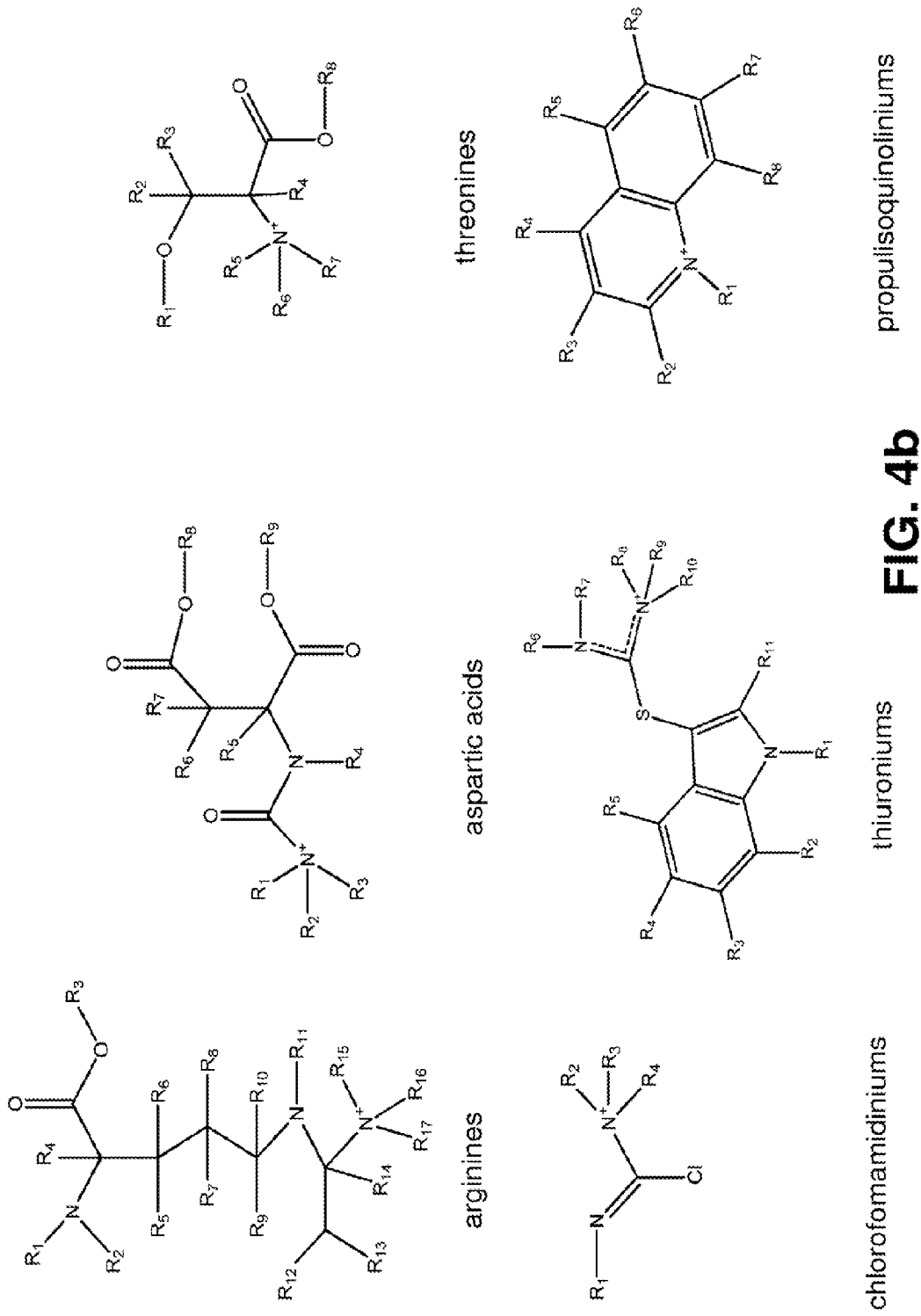
Figure 4C:
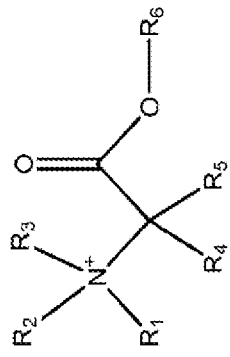
Figure 4C:
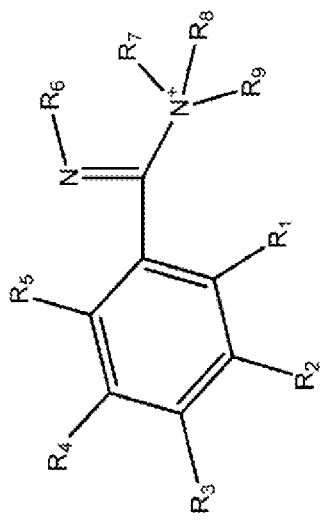
Figure 4C:
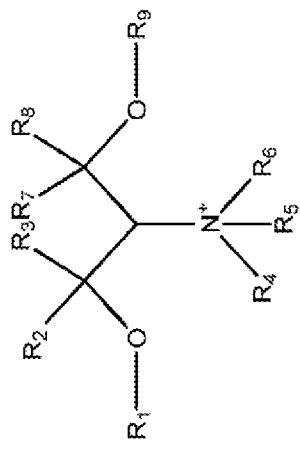
Figure 4C:
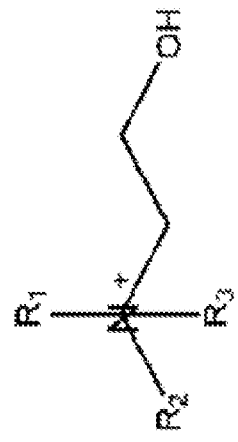
Figure 5A:
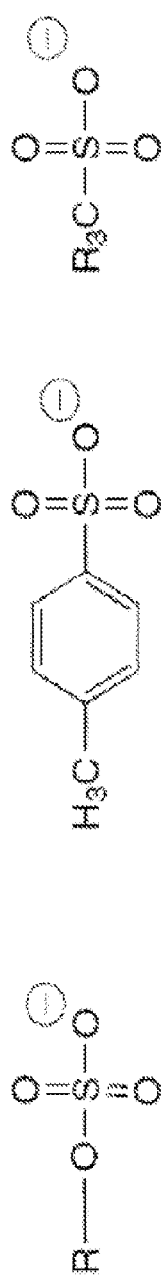
FIGS. 5a and 5b illustrate some of the anions that may help to stabilize the $(CO_2)^-$ anion.
Figure 5A:
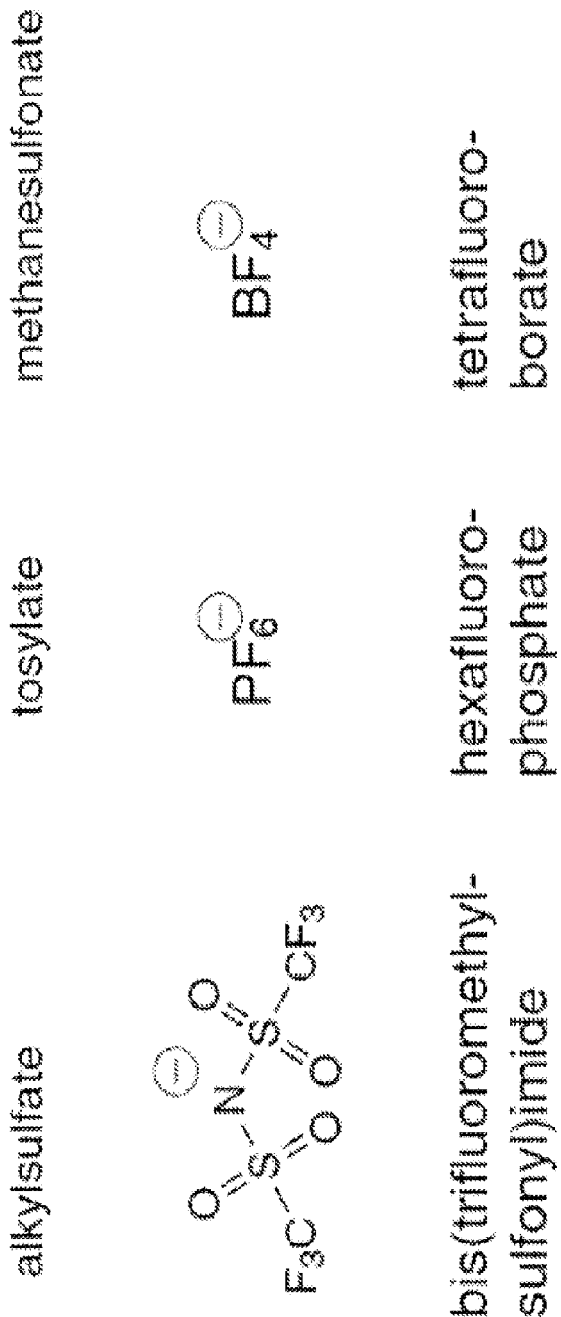
Figure 5B:
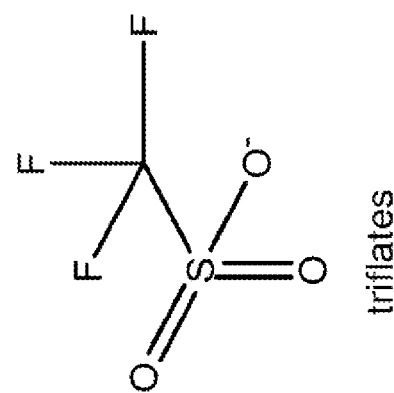
Figure 5B:
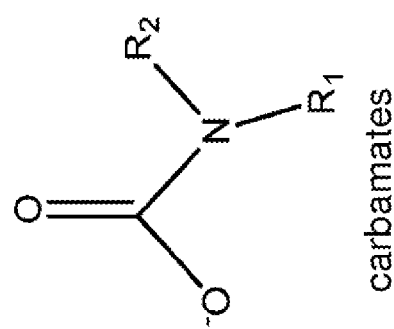
Figure 5B:
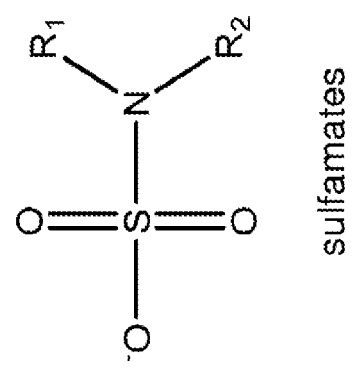
Figure 6:
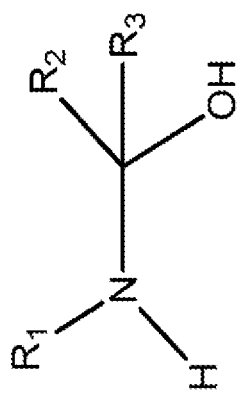
FIG. 6 illustrates some of the neutral molecules that may be used to form a complex with $(CO_2)^-$.
Figure 6:
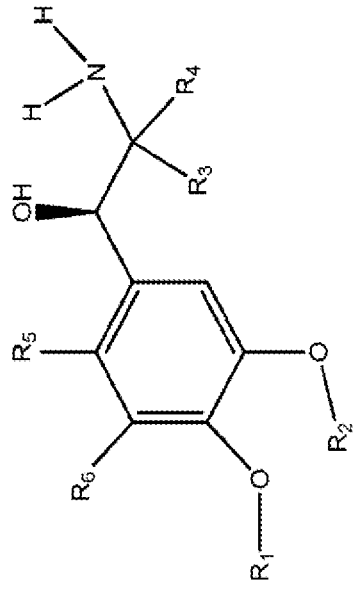
Figure 6:
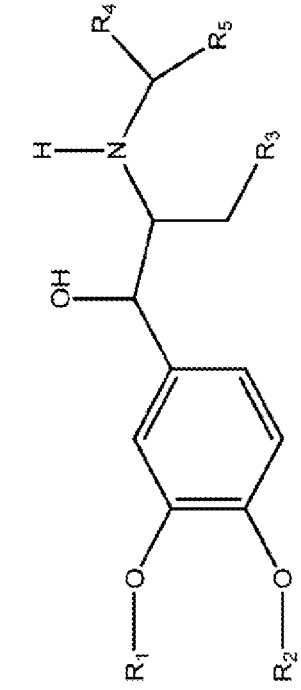

Solutions that include one or more of the cations in FIGS. 4a, 4b and 4c, the anions in FIGS. 5a and 5b, and/or the neutral species in FIG. 6, where R1, R2 and R3 (and R4-R17) include H, OH or any ligand containing at least one carbon atom, are believed to form complexes with $CO_2$ or $(CO_2)^-$. Specific examples include: imidazoliums (also called imidazoniums), pyridiniums, pyrrolidiniums, phosphoniums, ammoniums, sulfoniums, prolinates, and methioninates. All of these examples might be able to be used as Helper Catalysts for $CO_2$ conversion, and are specifically included in the invention. These examples are meant for illustrative purposes only, and are not meant to limit the scope of the invention.

In general one can determine whether a given substance S is a Helper Catalyst for a reaction R catalyzed by an active metal M as follows:

Fill a standard 3 electrode electrochemical cell with the electrolyte commonly used for reaction R. Common electrolytes include such as 0.1 M sulfuric acid or 0.1 M KOH in water can also be used.

Mount the active metal into the 3 electrode electrochemical cell and an appropriate counter electrode.

Run several CV cycles to clean the active metal.

Measure the reversible hydrogen electrode (RHE) potential in the electrolyte

Load the reactants for the reaction R into the cell, and measure a CV of the reaction R, noting the potential of the peak associated with the reaction R.

Calculate V1=the difference between the onset potential of the peak associated with reaction and RHE.

Calculate V1A=the difference between the maximum potential of the peak associated with reaction and RHE.

Add 0.0001 to 99.9999% of the substance S to the electrolyte.

Measure RHE in the reaction with Helper Catalyst.

Measure the CV of reaction R again, noting the potential of the peak associated with the reaction R.

Calculate V2=the difference between the onset potential of the peak associated with reaction and RHE.

Calculate V2A=the difference between the maximum potential of the peak associated with reaction and RHE.

If V2<V1 or V2A<V1A at any concentration of the substance S between 0.0001 and 99.9999%, the substance S is a Helper Catalyst for the reaction.

Further, the Helper Catalyst could be in any one of the following forms: (i) a solvent for the reaction; (ii) an electrolyte; (iii) an additive to any component of the system; or (iv)

something that is bound to at least one of the catalysts in a system. These examples are meant for illustrative purposes only, and are not meant to limit the scope of the invention.

Those trained in the state of the art should recognize that one might only need a tiny amount of the Helper Catalyst to have a significant effect. Catalytic reactions often occur on distinct active sites. The active site concentration can be very low, so in principle a small amount of Helper Catalyst can have a significant effect on the rate. One can obtain an estimate of how little of the Helper Catalyst would be needed to change the reaction from Pease, et al., JACS 47, 1235 (1925) study of the effect of carbon monoxide (CO) on the rate of ethylene hydrogenation on copper. This paper is incorporated into this disclosure by reference. Pease, et al., found that 0.05 cc's (62 micrograms) of carbon monoxide (CO) was sufficient to almost completely poison a 100 gram catalyst towards ethylene hydrogenation. This corresponds to a poison concentration of 0.0000062% by weight of CO in the catalyst. Those trained in the state of the art know that if 0.0000062% by weight of the poison in a Catalytically Active Element-poison mixture could effectively suppress a reaction, then as little as 0.0000062% by weight of Helper Catalyst in an Active Element, Helper Catalyst Mixture could enhance a reaction. This provides an estimate of a lower limit to the Helper Catalyst concentration in an Active Element, Helper Catalyst Mixture.

The upper limit is illustrated in Example 1 below, where the Active Element, Helper Catalyst Mixture could have approximately 99.999% by weight of Helper Catalyst, and the Helper Catalyst could be at least an order of magnitude more concentrated. Thus the range of Helper Catalyst concentrations for the invention here may be 0.0000062% to 99.9999% by weight.

FIG. 3 only considered the electrochemical conversion of $CO_2$, but the method is general. There are many examples where energy is needed to create a key intermediate in a reaction sequence. Examples include: homogeneously catalyzed reactions, heterogeneously catalyzed reactions, chemical reactions in chemical plants, chemical reactions in power plants, chemical reactions in pollution control equipment and devices, chemical reactions in safety equipment, chemical reactions in fuel cells, and chemical reactions in sensors. Theoretically, if one could find a Helper Catalyst that forms a complex with a key intermediate, the rate of the reaction should increase. All of these examples are within the scope of the invention.

Specific examples of specific processes that may benefit with Helper Catalysts include the electrochemical process to produce products including one or more of $Cl_2$, $Br_2$, $I_2$, NaOH, KOH, NaClO, $NaClO_3$, $KClO_3$, $CF_3COOH$.

Further, the Helper Catalyst could enhance the rate of a reaction even if it does not form a complex with a key intermediate. Examples of possible mechanisms of action include the Helper Catalyst (i) lowering the energy to form a key intermediate by any means, (ii) donating or accepting electrons or atoms or ligands, (iii) weakening bonds or otherwise making them easier to break, (iv) stabilizing excited states, (v) stabilizing transition states, (vi) holding the reactants in close proximity or in the right configuration to react, or (vii) blocking side reactions. Each of these mechanisms is described on pages 707 to 742 of Masel, Chemical Kinetics and Catalysis, Wiley, NY (2001). All of these modes of action are within the scope of the invention.

Also, the invention is not limited to just the catalyst. Instead it includes any process or device that uses an Active Element, Helper Catalyst Mixture as a catalyst. Fuel cells are sensors are specifically included in the invention.

Without further elaboration, it is believed that one skilled in the art using the preceding description can utilize the invention to the fullest extent. The following examples are illustrative only, and not limiting of the disclosure in any way whatsoever. These are merely illustrative and are not meant to be an exhaustive list of all possible embodiments, applications or modifications of the invention.

Specific Example 1

Figure 7:
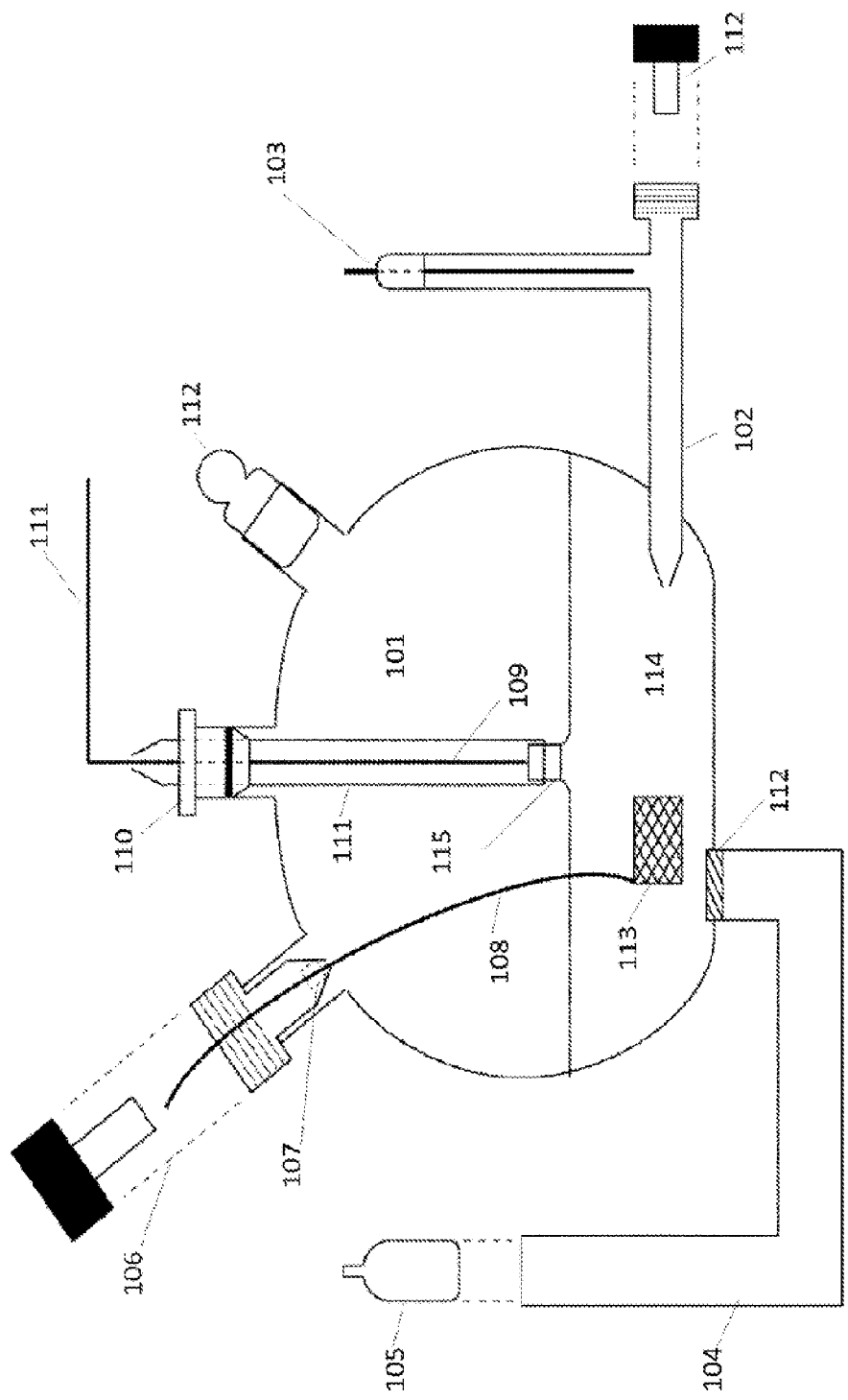
FIG. 7 shows a schematic of a cell used for the experiments in Examples 1, 2, 3, 4 and 5.

Using an Active Element, Helper Catalyst Mixture Including Platinum and 1-Ethyl-3-Methylimidazolium Tetrafluoroborate (EMIM-BF4) to Lower the Overpotential for Electrochemical Conversion of $CO_2$ and Raise the Selectivity (Current Efficiency) of the Reaction The experiments used the glass three-electrode cell shown in FIG. 7. The cell consisted of a three-neck flask 101, to hold the anode 108, and the cathode 109. A silver/0.01 molar silver ion reference electrode 103 in acetonitrile was connected to the cell through a Luggin Capillary 102. The reference electrode 103 was fitted with a Vycor® frit to prevent any of the reference electrode solution from contaminating the ionic liquid in the capillary. The reference electrode was calibrated against the ferrocene Fc/Fc+ redox couple. A conversion factor of +535 mV was used to convert our potential axis to reference the Standard Hydrogen Electrode (SHE). A 25×25 mm platinum gauze (size 52) 113 was connected to the anode while a 0.33 $cm^2$ polycrystalline gold plug 115 was connected to the cathode.

Prior to the experiments all glass parts were put through a 1% Nochromix® bath (2 hours), followed by a 50/50 v/v Nitric Acid/Water bath (12 hours), followed by rinsing with Millipore water. In addition the gold plug 115 and platinum gauze 113 were mechanically polished using procedures known to workers trained in the art. They were then cleaned in a sulfuric acid bath for 12 hours.

During the experiment a catalyst ink comprising a Catalytically Active Element, platinum, was first prepared as follows: First 0.056 grams of Johnson-Matthey Hispec 1000 platinum black purchased from Alfa-Aesar was mixed with 1 gram of Millipore water and sonicated for 10 minutes to produce a solution containing a 5.6 mg/ml suspension of platinum black in Millipore water. A 25 µl drop of the ink was placed on the gold plug 115 and allowed to dry under a heat lamp for 20 min, and subsequently allowed to dry in air for an additional hour. This yielded a catalyst with 0.00014 grams of Catalytically Active Element, platinum, on a gold plug. The gold plug was mounted into the three neck flask 101. Next a Helper Catalyst, EMIM-BF4 (EMD Chemicals, Inc., San Diego, Calif., USA) was heated to 120° C. under a −23 in. Hg vacuum for 12 hours to remove residual water and oxygen. The concentration of water in the ionic liquid after this procedure was found to be ca. 90 mM by conducting a Karl-Fischer titration. (That is, the ionic liquid contained 99.9999% of Helper Catalyst.) 13 grams of the EMIM-BF4 was added to the vessel, creating an Active Element, Helper Catalyst Mixture that contained about 99.999% of the Helper Catalyst. The geometry was such that the gold plug formed a meniscus with the EMIM-BF4 Next ultra-high-purity (UHP) argon was fed through the sparging tube 104 and glass frit 112 for 2 hours at 200 sccm to further remove any moisture picked up by contact with the air.

Next the cathode was connected to the working electrode connection in an SI 1287 Solartron electrical interface, the anode was connected to the counter electrode connection and the reference electrode was connected to the reference electrode connection on the Solartron. Then the potential on the cathode was swept from −1.5 V versus a standard hydrogen electrode (SHE) to 1V vs. SHE, and then back to −1.5 volts versus SHE thirty times at a scan rate of 50 mV/s. The current produced during the last scan is labeled as the "argon" scan in FIG. 8.

Next carbon dioxide was bubbled through the sparging tube at 200 sccm for 30 minutes, and the same scanning technique was used. That produced the $CO_2$ scan in FIG. 8. Notice the peak starting at −0.2 volts with respect to SHE, and reaching a maximum at −0.4 V with respect to SHE. That peak is associated with $CO_2$ conversion.

We have also used broad-band sum frequency generation (BB-SFG) spectroscopy to look for products of the reaction. We only detect our desired product carbon monoxide in the voltage range shown (namely, the selectivity is about 100%). Oxalic acid is detected at higher potentials.

Table 1 compares these results to results from the previous literature. The table shows the actual cathode potential. More negative cathode potentials correspond to higher overpotentials. More precisely the overpotential is the difference between the thermodynamic potential for the reaction (about −0.2 V with respect to SHE) and the actual cathode potential. The values of the cathode overpotential are also given in the table. Notice that the addition of the Helper Catalyst has reduced the cathode overpotential (namely, lost work) on platinum by a factor of 4.5 and improved the selectivity to nearly 100%.

TABLE 1

(Comparison of data in Example 1 to results reported in previous literature)

| Reference | Catalytically Active Element | Cathode potential versus SHE | Cathode overpotential | Selectivity to carbon-containing products |
|---|---|---|---|---|
| Data from Example 1 | Platinum (+EMIM-BF4) | −0.4 V | 0.2 V | ~100% |
| Hori Review Table 3 | Platinum (+water) | −1.07 V | 0.87 V | 0.1% |
| The Li and Oloman papers and the '727 application | Tin | −2.5 to −3.2 V | 2.3 to 3 V | 40-70% |

TABLE 2

(Cathode potentials where $CO_2$ conversion starts on a number of Catalytically Active Elements as reported in the Hori Review)

| Metal | Cathode potential (SHE) | Metal | Cathode potential (SHE) | Metal | Cathode potential (SHE) |
|---|---|---|---|---|---|
| Pb | −1.63 | Hg | −1.51 | Ti | −1.60 |
| In | −1.55 | Sn | −1.48 | Cd | −1.63 |
| Bi | −1.56 | Au | −1.14 | Ag | −1.37 |
| Zn | −1.54 | Pd | −1.20 | Ga | −1.24 |
| Cu | −1.44 | Ni | −1.48 | Fe | −0.91 |
| Pt | −1.07 | Ti | −1.60 | | |

Figure 8:
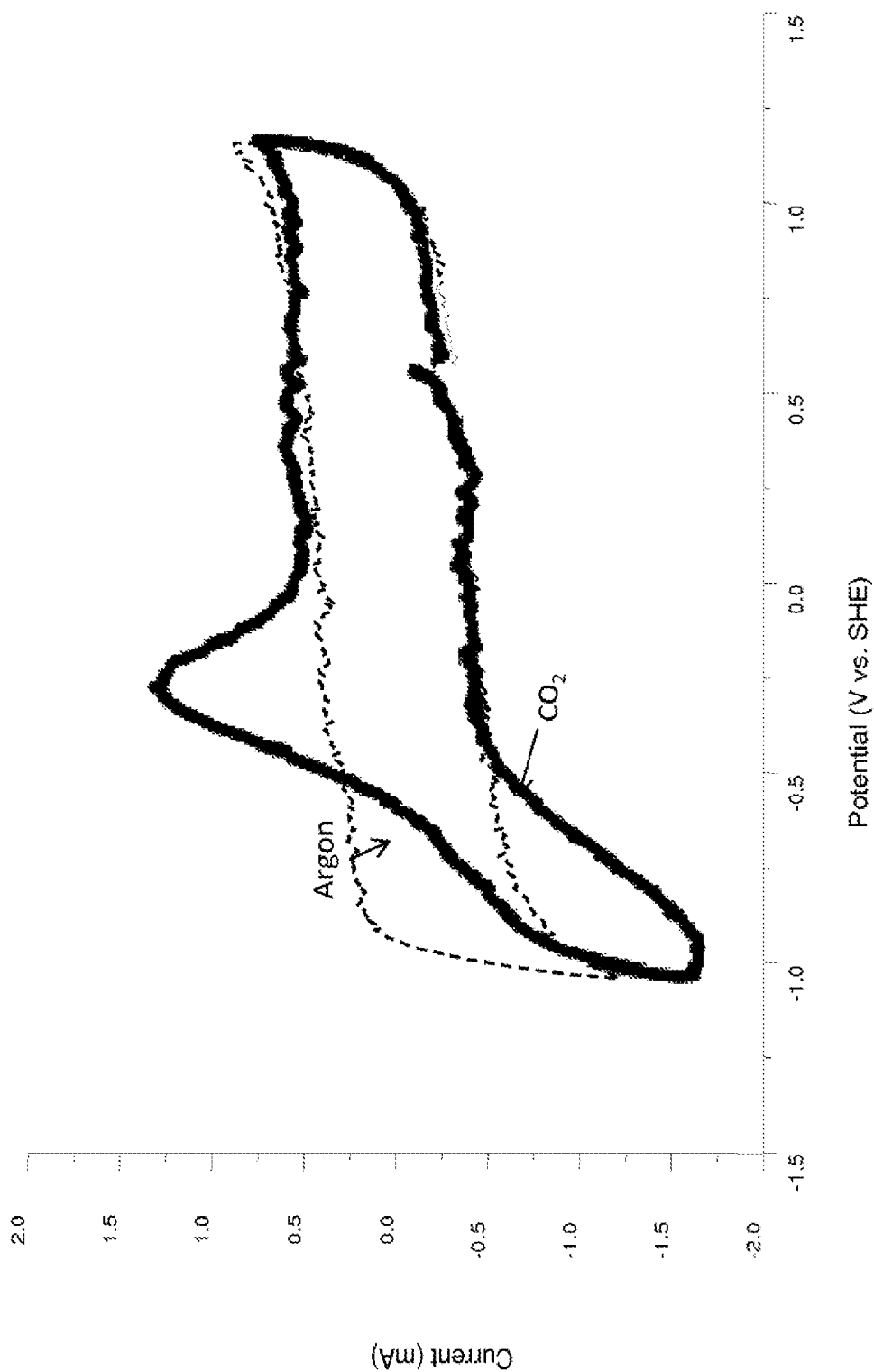
FIG. 8 represents a comparison of the cyclic voltammetry for a blank scan where the catalyst was synthesized as in Example 1 where (i) the EMIM-BF4 was sparged with argon, and (ii) a scan where the EMIM-BF4 was sparged with $CO_2$. Notice the large negative peak associated with $CO_2$ complex formation.

Table 2 indicates the cathode potential needed to convert $CO_2$. Notice that all of the values are more negative than −0.9 V. By comparison, FIG. 8 shows that $CO_2$ conversion starts at −0.2 V with respect to the reversible hydrogen electrode (RHE) when the Active Element, Helper Catalyst Mixture is used as a catalyst. More negative cathode potentials correspond to higher overpotentials. This is further confirmation that Active Element, Helper Catalyst Mixtures are advantageous for $CO_2$ conversion.

Figure 9:
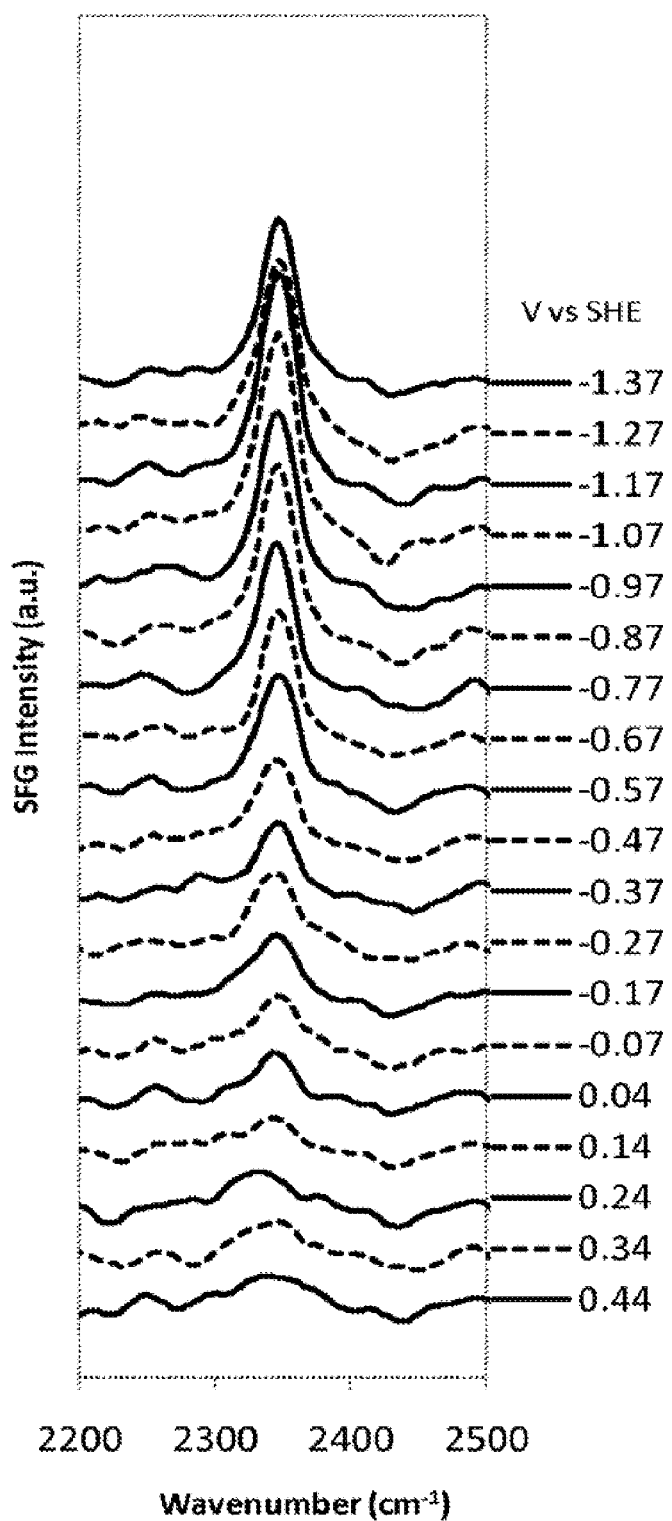
FIG. 9 represents a series of Broad Band Sum Frequency Generation (BB-SFG) spectra taken sequentially as the potential in the cell was scanned from +0.0 to −1.2 with respect to SHE.

FIG. 9 shows a series of BB-SFG spectra taken during the reaction. Notice the peak at 2350 $cm^{-1}$. This peak corresponded to the formation of a stable complex between the Helper Catalyst and $(CO_2)^-$. It is significant that the peak starts at −0.1 V with respect to SHE. According to the Hori Review, $(CO_2)^-$ is thermodynamically unstable unless the potential is more negative than −1.2 V with respect to SHE on platinum. Yet FIG. 9 shows that the complex between EMIM-BF4 and $(CO_2)^-$ is stable at −0.1 V with respect to SHE.

Those trained in the art should recognize that this result is very significant. According to the Hori Review, the Dubois Review and references therein, the formation of $(CO_2)^-$ is the rate determining step in $CO_2$ conversion to CO, OH—, HCO—, $H_2CO$, $(HCO_2)$—, $H_2CO_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, and $(COO^-)_2$ on V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd. The $(CO_2)^-$ is thermodynamically unstable at low potentials, which leads to a high overpotential for the reaction as indicated in FIG. 2. The data in FIG. 9 shows that one can form the EMIM-BF4-$(CO_2)^-$ complex at low potentials. Thus, the reaction can follow a low energy pathway for $CO_2$ conversion to CO, $OH^-$, $HCO^-$, $H_2CO$, $(HCO_2)^-$, $H_2CO_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, or $(COO^-)_2$ on V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd as indicated in FIG. 3.

In order to understand the economic consequences of this result, we calculated the cost of the electricity needed to create 100,000 metric tons per year of formic acid via two processes, (i) the process described in The Li and Oloman papers and the '727 application, and (ii) a similar process using the catalyst in this example. In both cases we assumed that the anode would run at +1.2 V with respect to SHE and that electricity would cost $0.06/kW-hr, and we scaled the current to be reasonable. The results of the calculations are given in Table 3. Notice that the calculations predict that the electricity cost will go down by almost a factor of 5 if the new catalysts are used. These results demonstrate the possible impact of the new catalysts disclosed here.

TABLE 3

(Comparison of the projected costs using catalyst in Li and Oloman papers and the '727 application, and a similar process using the catalyst in this example)

| Catalyst | Cathode potential, V (SHE) | Anode Potential, V (SHE) | Net Potential V | Selectivity | Yearly Electricity cost |
|---|---|---|---|---|---|
| The Li and Oloman papers and the '727 application | −3.2 | 1.2 | 4.4 | 0.6 | $65,000,000 |
| Active Element, Helper Catalyst Mixture | −0.4 | 1.2 | 1.6 | 1 | $14,000,000 |

Specific Example 2

The Effect of Dilution on the Electrochemical Conversion of $CO_2$

Figure 10:
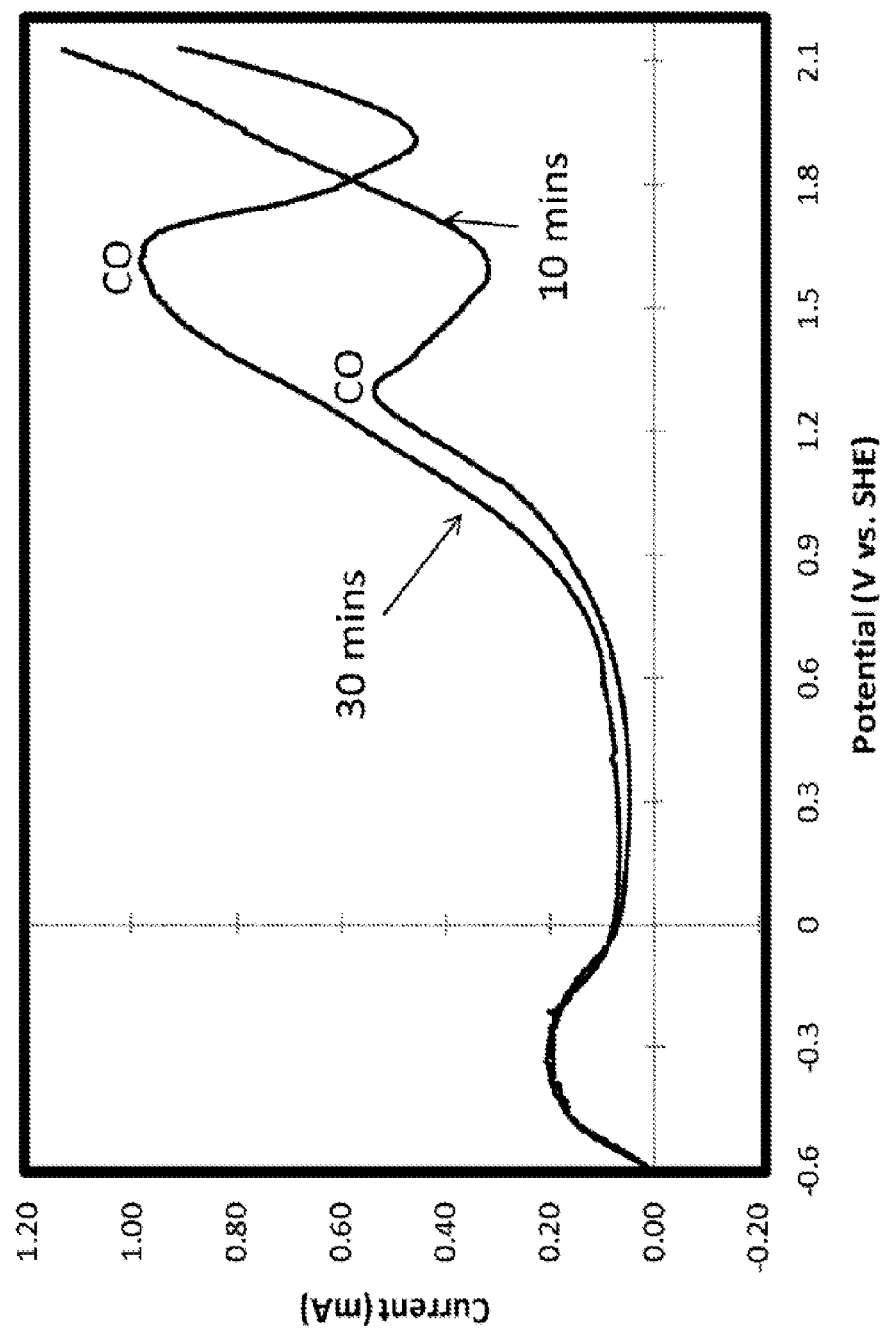
FIG. 10 shows a CO stripping experiment done by holding the potential at −0.6 V for 10 or 30 minutes and then measuring the size of the CO stripping peak between 1.2 and 1.5 V with respect to RHE.

This example shows that water additions speed the formation of CO. The experiment used the Cell and procedures in Example 1, with the following exception: a solution containing 98.55% EMIM-BF4 and 0.45% water was substituted for the 99.9999% EMIM-BF4 used in Example 1, the potential was held for 10 or 30 minutes at −0.6 V with respect to RHE, and then the potential was ramped positively at 50 mV/sec. FIG. 10 shows the result. Notice the peak between 1.2 and 1.5 V. This is the peak associated with CO formation and is much larger than in Example 1. Thus the addition of water has accelerated the formation of CO presumably by acting as a reactant.

Specific Example 3

Using an Active Element, Helper Catalyst Mixture Including Palladium and Choline Iodide to $CO_2$ Lower the Overpotential for Electrochemical Conversion of $CO_2$ in Water The next example is to demonstrate that the invention can be practiced using palladium as an Active Element and choline iodide as a Helper Catalyst.

The experiment used the Cell and procedures in Example 1, with the following exceptions: (i) a 10.3% by weight of a Helper Catalyst, choline iodide, in water solution was substituted for the 1-ethyl-3-methylimidazolium tetrafluoroborate and (ii) a 0.25 cm$^2$ Pd foil purchased from Alfa Aesar of Ward Hill, Mass., USA, was substituted for the gold plug and platinum black on the cathode, and a silver/silver chloride reference was used.

The cell contained 52 mg of palladium and 103 mg of Helper Catalyst, so the overall catalyst mixture contained 66% of Helper Catalyst.

Figure 11:
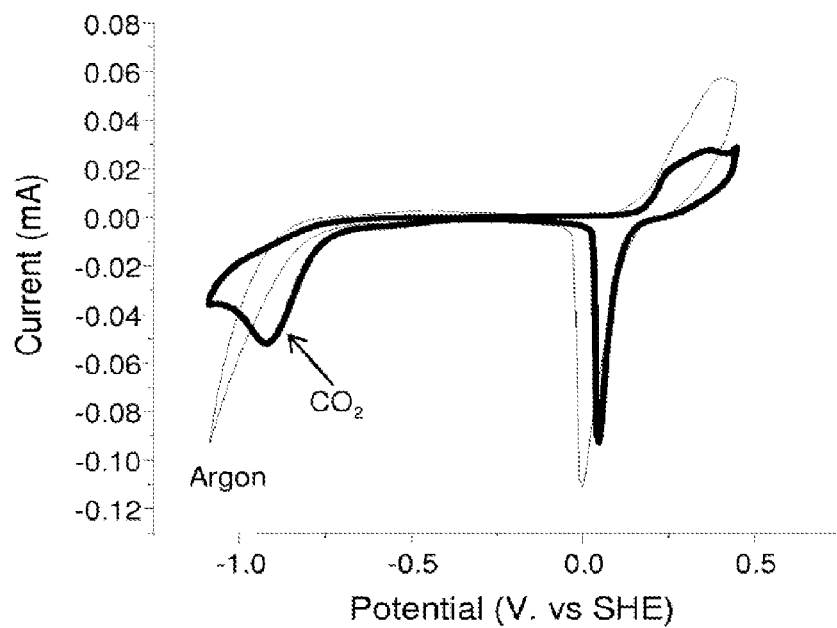
FIG. 11 represents a comparison of the cyclic voltammetry for a blank scan where the catalyst was synthesized as in Example 3 where (i) the water-choline iodide mixture was sparged with argon and (ii) a scan where the water-choline iodide mixture was sparged with $CO_2$.

FIG. 11 shows a CV taken under these conditions. There is a large negative peak near zero volts with respect to SHE associated with iodine transformations and a negative going peak at about 0.8 V associated with conversion of $CO_2$. By comparison the data in Table 2 indicates that one needs to use a voltage more negative than −1.2 V to convert $CO_2$ on palladium in the absence of the Helper Catalyst. Thus, the Helper Catalyst has lowered the overpotential for $CO_2$ formation by about 0.5 V.

This example also demonstrates that the invention can be practiced with a second Active Element, palladium, and a second Helper Catalyst, choline iodide. Further, those trained in the state of the art will note that there is nothing special about the choice of palladium and choline iodide. Rather, this example shows that the results are general and not limited to the special case in Example 1.

Specific Example 4

Using an Active Element, Helper Catalyst Mixture that Includes Palladium and Choline Chloride to Lower the Overpotential for Electrochemical Conversion of $CO_2$ to Formic Acid The next example is to demonstrate that the invention can be practiced using a third Helper Catalyst, choline chloride.

The experiment used the Cell and procedures in Example 3, with the following exception: a 6.5% by weight choline chloride in water solution was substituted for the choline iodide solution.

Figure 12:
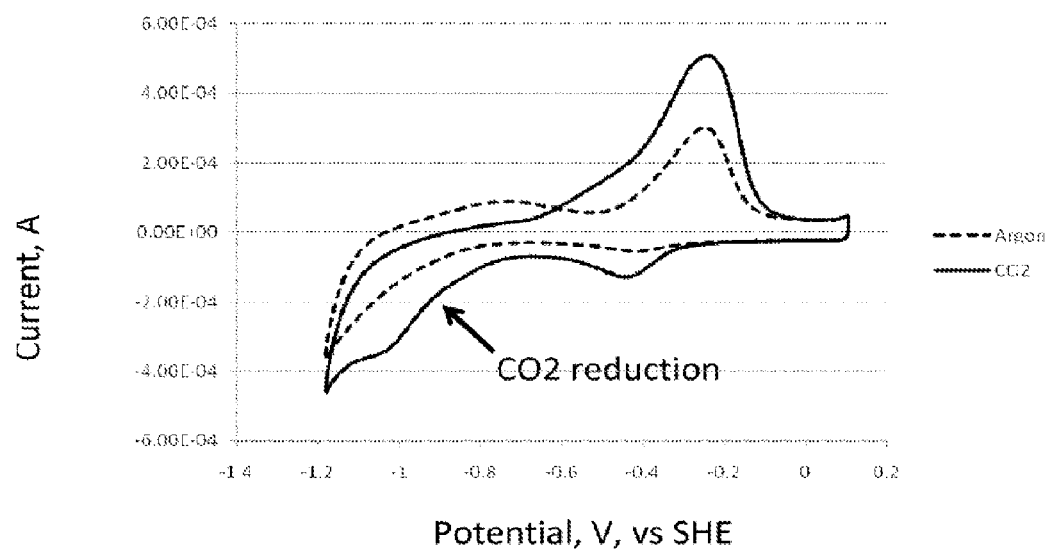
FIG. 12 shows a comparison of the cyclic voltammetry for a blank scan where the catalyst was synthesized as in Example 4 where (i) the water-choline chloride mixture was sparged with argon and (ii) a scan where the water-choline chloride mixture was sparged with $CO_2$.

The cell contained 52 mg of palladium and 65 mg of Helper Catalyst, so the overall catalyst mixture contained 51% of Helper Catalyst. FIG. 12 shows a comparison of the cyclic voltammetry for a blank scan where (i) the water-choline chloride mixture was sparged with argon and (ii) a scan where the water-choline chloride mixture was sparged with $CO_2$. Notice the negative going peaks starting at about −0.6. This shows that $CO_2$ is being reduced at −0.6 V. By comparison the data in Table 2 indicates that a voltage more negative than −1.2 V is needed to convert $CO_2$ on palladium in the absence of the Helper Catalyst. Thus, the overpotential for $CO_2$ conversion has been lowered by 0.6 V by the Helper Catalyst.

Another important point is that there is no strong peak for hydrogen formation. A bare palladium catalyst would produce a large hydrogen peak at about −0.4 V at a pH of 7, while the hydrogen peak moves to −1.2 V in the presence of the Helper Catalyst. The Hori Review reports that palladium is not an effective catalyst for $CO_2$ reduction because the side reaction producing hydrogen is too large. The data in FIG. 12 show that the Helper Catalysts are effective in suppressing hydrogen formation.

We have also used CV to analyze the reaction products. Formic acid was the only product detected. By comparison, the Hori Review reports that the reaction is only 2.8% selective to formic acid in water. Thus the Helper Catalyst has substantially improved the selectivity of the reaction to formic acid.

This example also demonstrates that the invention can be practiced with a third Helper Catalyst, choline chloride. Further, those trained in the state of the art will note that there is nothing special about the choice of palladium and choline chloride. Rather, this example shows that the results are general and not limited to the special case in Example 1.

Further, those trained in the state of art should recognize that the results should not depend on the thickness of the palladium foil. For example if we increase the thickness of the palladium foil by a factor of 10, the Active Element-Helper Catalyst mixture would only contain 11% of Helper Catalyst. If the foil thickness is increased to 0.5 inches, the mixture will contain about 1% of Helper Catalyst.

Specific Example 5

Using an Active Element, Helper Catalyst Mixture that Includes Nickel and Choline Chloride to Lower the Overpotential for Electrochemical Conversion of $CO_2$ to CO The next example is to demonstrate that the invention can be practiced using a third metal, nickel.

The experiment used the Cell and procedures in Example 4, with the following exception: a nickel foil from Alfa Aesar was substituted for the palladium foil.

Figure 13:
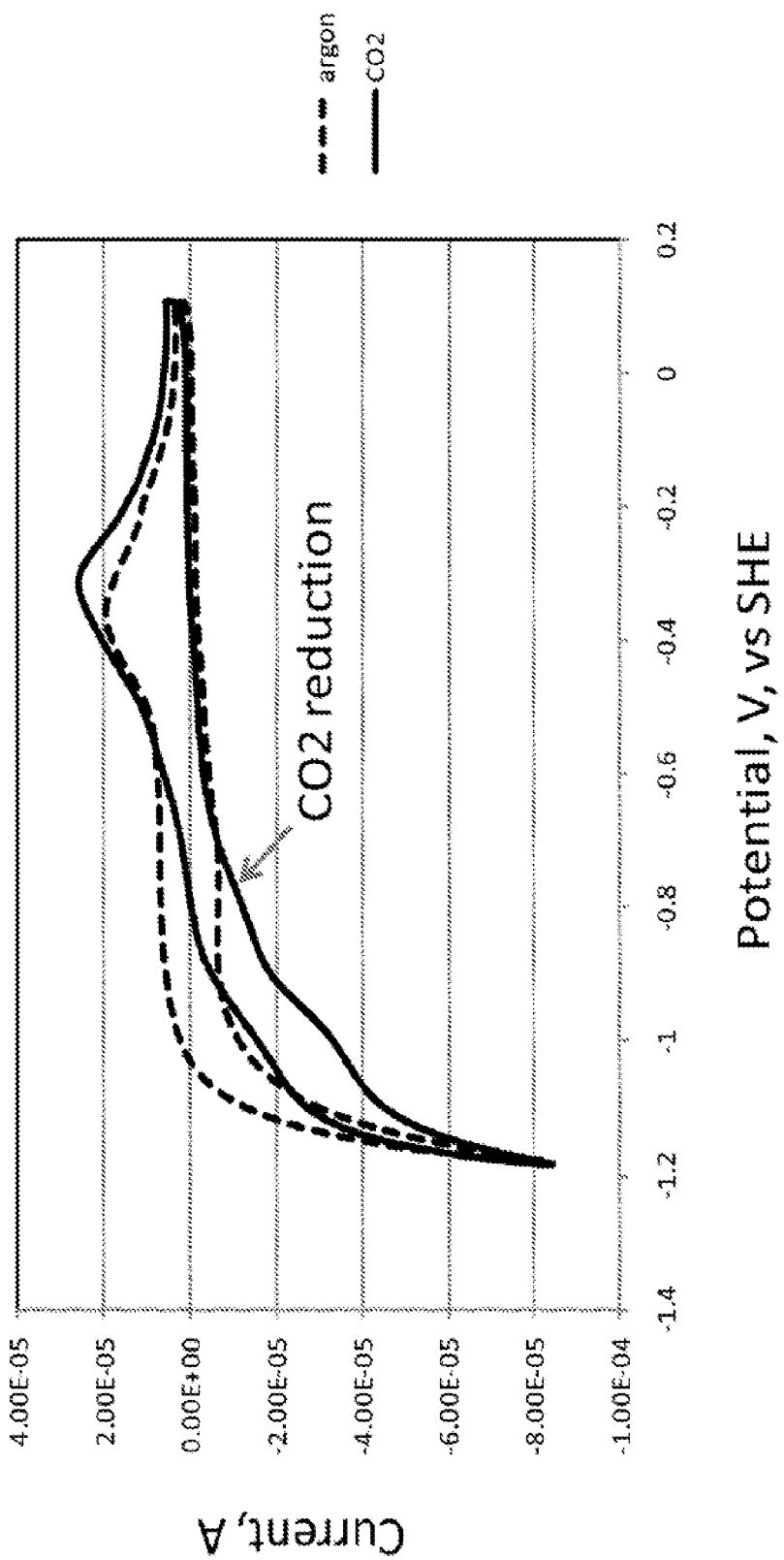
FIG. 13 shows a comparison of the cyclic voltammetry for a blank scan where the catalyst was synthesized as in Example 5 where (i) the water-choline chloride mixture was sparged with argon and (ii) a scan where the water-choline chloride mixture was sparged with $CO_2$.

FIG. 13 shows a comparison of the cyclic voltammetry for a blank scan where (i) the water-choline chloride mixture was sparged with argon and (ii) a scan where the water-choline chloride mixture was sparged with $CO_2$. Notice the negative going peaks starting at about −0.6. This shows that $CO_2$ is being reduced at −0.6 V. By comparison, the data in Table 2 indicates that a voltage more negative than −1.48 V is needed to convert $CO_2$ on nickel in the absence of the Helper Catalyst. Thus, the Helper Catalyst has lowered the overpotential for $CO_2$ conversion.

Another important point is that there is no strong peak for hydrogen formation. A bare nickel catalyst would produce a large hydrogen peak at about −0.4 V at a pH of 7, while the hydrogen peak moves to −1.2 V in the presence of the Helper Catalyst. The Hori Review reports that nickel is not an effective catalyst for $CO_2$ reduction because the side reaction producing hydrogen is too large. The data in FIG. 13 show that the Helper Catalysts are effective in suppressing hydrogen formation.

Also the Helper Catalyst is very effective in improving the selectivity of the reaction. The Hori Review reports that hydrogen is the major product during carbon dioxide reduction on nickel in aqueous solutions. The hydrolysis shows 1.4% selectivity to formic acid, and no selectivity to carbon monoxide. By comparison, analysis of the reaction products by CV indicates that carbon monoxide is the major product during $CO_2$ conversion on nickel in the presence of the Helper Catalyst. There may be some formate formation. However, no hydrogen is detected. This example shows that the Helper Catalyst has tremendously enhanced the selectivity of the reaction toward CO and formate.

This example also demonstrates that the invention can be practiced with a third metal, nickel. Further, those trained in the state of the art will note that there is nothing special about the choice of nickel and choline chloride. Rather, this example shows that the results are general and not limited to the special case in Example 1.

Those trained in the state of art should realize that since choline chloride and choline iodide are active, other choline salts such as choline bromide, choline fluoride and choline acetate should be active too.

Specific Example 6

Demonstration that an Active Element (Gold), Helper Catalyst Mixture is Useful in a $CO_2$ Sensor This example demonstrates that the invention can be practiced with a fourth Active Element, gold. It also demonstrates that the catalysts are useful in sensors.

The sensor may be a simple electrochemical device wherein an Active Element, Helper Catalyst Mixture is placed on an anode and cathode in an electrochemical device, then the resistance of the sensor is measured. If there is no $CO_2$ present, the resistance will be high, but preferably not infinite, because of leakage currents. When $CO_2$ is present, the Active Element, Helper Catalyst Mixture may catalyze the conversion of $CO_2$. That allows more current to flow through the sensor. Consequently, the sensor resistance decreases. As a result, the sensor may be used to detect carbon dioxide.

An example sensor was fabricated on a substrate made from a 100 mm silicon wafer (Silicon Quest International, Inc., Santa Clara, Calif., USA, 500 μm thick, <100> oriented, 1-5 Ω-cm nominal resistivity) which was purchased with a 500 nm thermal oxide layer. On the wafer, 170 Å of chromium was deposited by DC magnetron sputtering (~$10^{-2}$ Torr of argon background pressure). Next, 1000 Å of a Catalytically Active Element, gold, was deposited on the chromium and the electrode was patterned via a standard lift-off photolithography process to yield the device shown schematically in FIG. 14.

Figure 14:
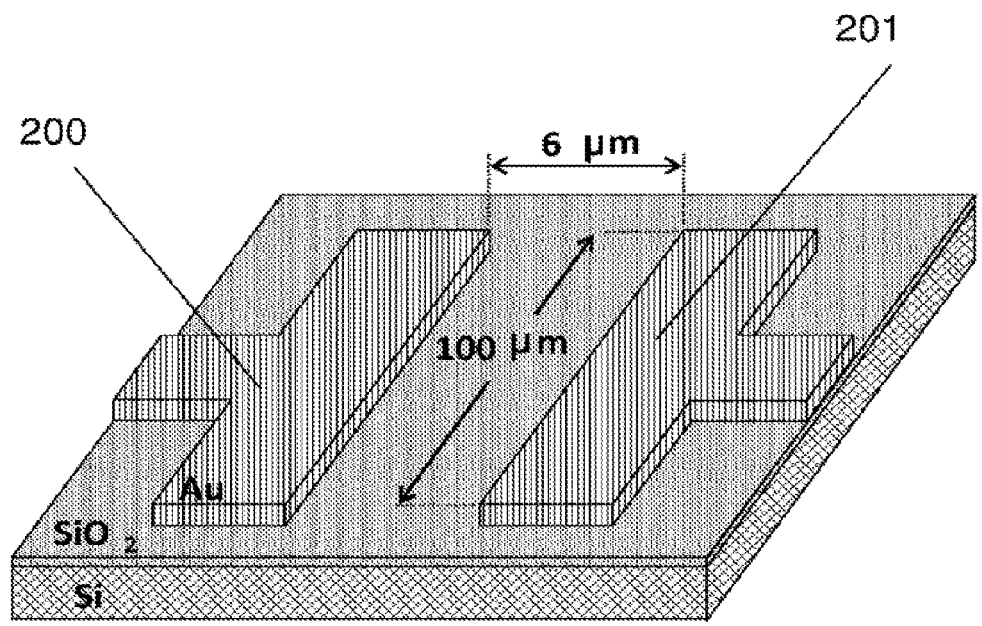
FIG. 14 shows a schematic of an example sensor before the Helper Catalyst was added.
Figure 15:
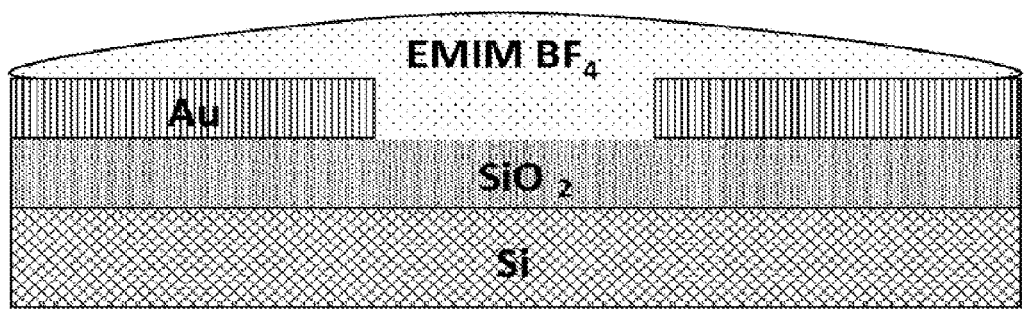
FIG. 15 shows a schematic of where EMIM BF4 is placed on the sensor.

At this point, the device consisted of an anode 200 and cathode 201 separated by a 6 μm gap (Note: FIGS. 14 and 15 do not include the reference numerals 200, 201, 202 or the mu symbol for μm.), wherein the anode and cathode were coated with a Catalytically Active Element, gold. At this point the sensor could not detect $CO_2$.

Next 2 μl of a Helper Catalyst, EMIM BF4 202 was added over the junction as shown in FIG. 15. The device was mounted into a sensor test cell with wires running from the anode and cathode.

Figure 16:
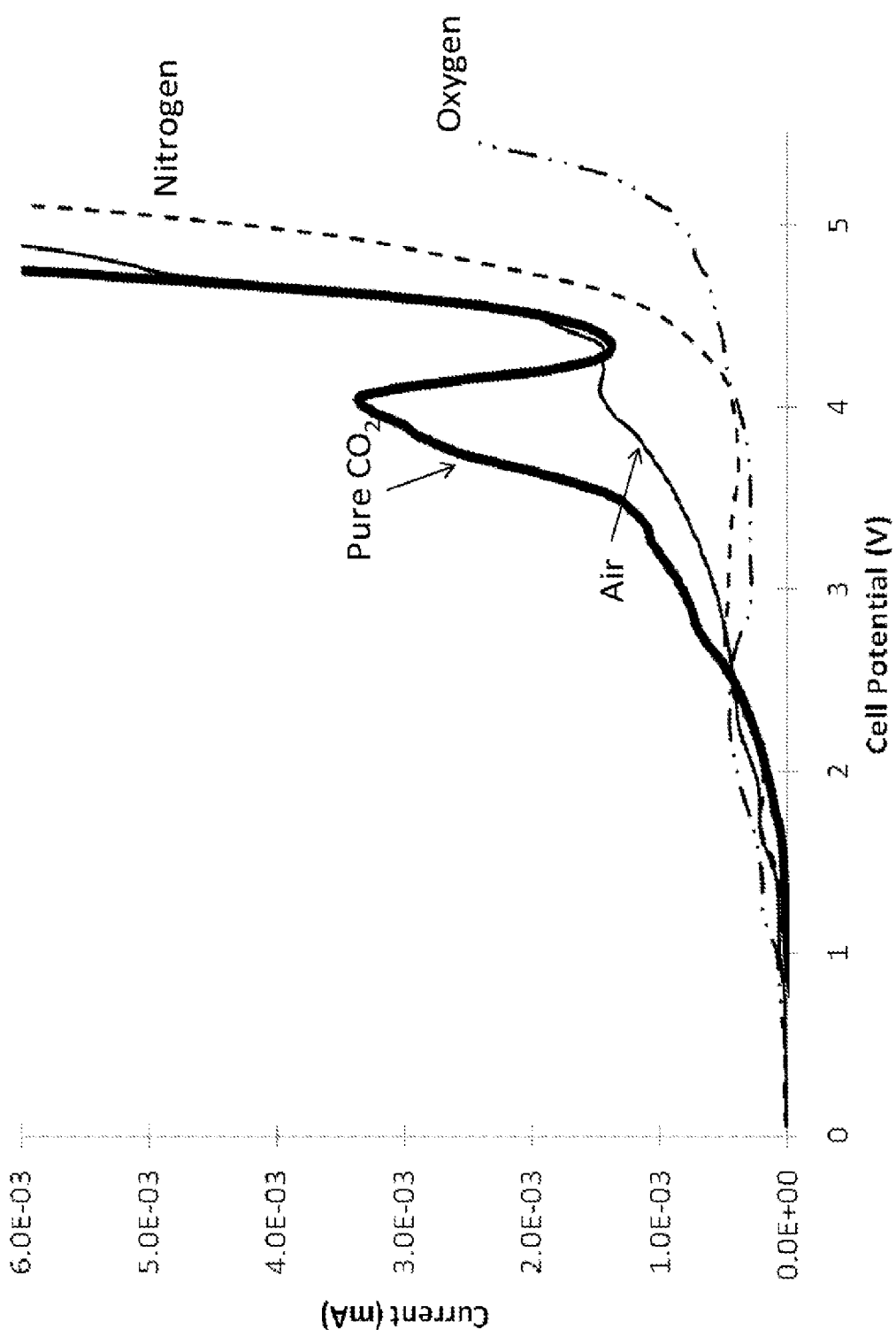
FIG. 16 represents the current measured when the voltage on the sensor was exposed to various gases; the applied voltage on the sensor was swept from 0 to 5 volts at 0.1 V/sec.

Next, the anode and cathode were connected to a SI 1287 Solartron electrical interface, and the catalysts were condition by sweeping from 0 volts to 5 volts at 0.1 V/sec and then back again. The process was repeated 16 times. Then the sensor was exposed to either nitrogen, oxygen, dry air or pure $CO_2$, and the sweeps were recorded. The last sweep is shown in FIG. 16. Notice that there is a sizable peak at an applied voltage of 4 volts in pure $CO_2$. That peak is associated with the electrochemical conversion of $CO_2$.

Notice that the peak is absent when the sensor is exposed to oxygen or nitrogen, but it is clearly seen when the sensor is exposed to air containing less than 400 ppm of $CO_2$. Further the peak grows as the $CO_2$ concentration increases. Thus, the sensor can be used to detect the presence of $CO_2$.

Figure 17:
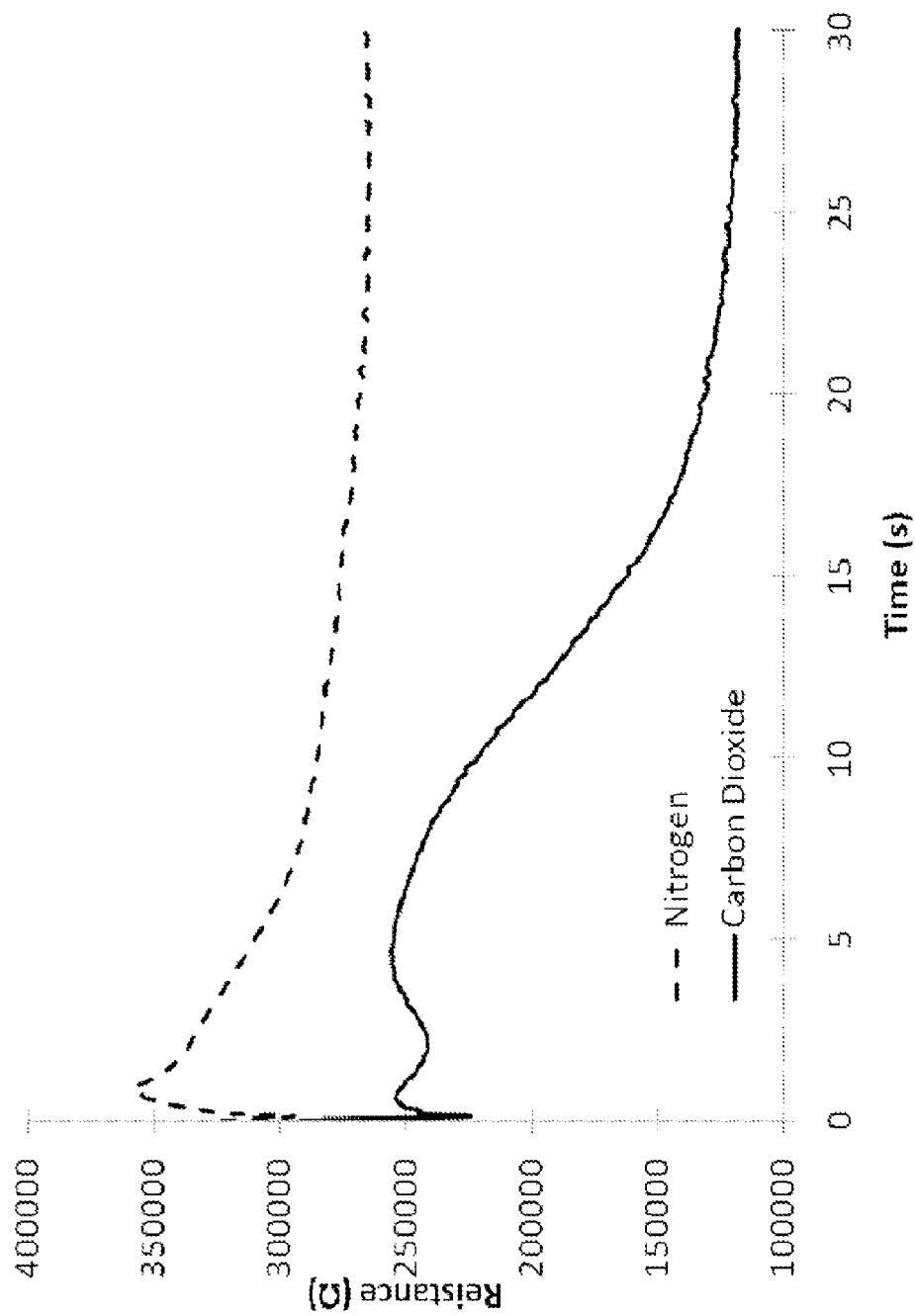
FIG. 17 represents the resistance of the sensor, in nitrogen and in carbon dioxide. The resistance was determined by measuring the voltage needed to maintain a current of 1 microamp. Time is the time from when the current was applied.

We have also run the sensor in a galvanastatic mode, where we measured the voltage needed to maintain the current constant at 1 microamp, and measured the voltage of the device. FIG. 17 shows that less voltage is needed to maintain the current when $CO_2$ is added to the cell. This shows that the sensor that includes an Active Element, Helper Catalyst Mixture responds to the presence of $CO_2$.

Table 4 compares the sensor here to those in the previous literature. Notice that the new sensor uses orders of magnitude less energy than commercial $CO_2$ sensors. This is a key advantage for many applications.

This example also illustrates that the invention can be practiced with a fourth Active Element, gold.

TABLE 4

(Comparison of power needed to run the present sensor to that needed to operate commercially available $CO_2$ sensors)

| Sensor | Power | Sensor | Power |
| --- | --- | --- | --- |
| Specific Example 6 | 5 × $10^{-7}$ watts | GE Ventostat 8100 | 1.75 watts |
| Honeywell C7232 | 3 watts | Vaisala CARBOCAP GMP343 | about 1 watt |

Specific Example 7

Steady State Production of Carbon Monoxide

This experiment used the flow cell described in T. Whipple, E. C. Finke, and P. J. A. Kenis, Electrochem. & Solid-State Lett., 2010, 13 (9), B109-B111 (the Whipple paper). First, catalyst inks were prepared as follows:

For the cathode: 10 mg of silver nanoparticles (Sigma Aldrich) was sonicated into a solution containing 100 μL of water, 100 μL of isopropyl alcohol and 5.6 μL of 5% Nafion (perfluorosulfonic acid) solution (Ion Power). The resultant catalyst ink was painted on a 1×1.5 cm section of a 2×3 cm piece of carbon paper (Ion Power) and dried with a heat lamp.

The preparation was identical for the anode except 4 mg of HiSpec 1000 platinum black (Sigma Adrich) was substituted for the silver.

Both catalysts were mounted in the flow cell described in the Whipple Paper. Five sccm of $CO_2$ was fed to the anode, and a solution containing 18 mole percent of EMIM-BF4 in water was fed into the gap between the anode and the cathode. At any one time the cell contained approximately 10 mg of silver nanoparticles and approximately 40 mg of EMIM-BF4 Helper Catalyst. A potential was applied to the cell, and the data in Table 5 were obtained. These results demonstrate that steady state production of useful products can be obtained with Catalytically Active Element-Helper Catalyst Mixtures.

TABLE 5

Products produced at various conditions

| Cathode potential Volts vs. RHE | Hydrogen production rate, μg/min | Carbon monoxide production rate, μg/min |
| --- | --- | --- |
| −0.358 | 0 | 0 |
| −0.862 | 1.1 | 2.6 |
| −1.098 | 1.4 | 50 |
| −1.434 | 1.1 | 250 |
| −1.788 | 0 | 560 |

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the chemical arts or in the relevant fields are intended to be within the scope of the appended claims.

The disclosures of all references and publications cited above are expressly incorporated by reference in their entireties to the same extent as if each were incorporated by reference individually.

While particular elements, embodiments and applications of the present invention have been shown and described, it will be understood, that the invention is not limited thereto, since modifications can be made by those skilled in the art without departing from the scope of the present disclosure, particularly in light of the foregoing teachings.

What is claimed is:

1. An electrocatalyst mixture comprising at least one Catalytically Active Element active for converting carbon dioxide ($CO_2$) to at least one reaction product and, as a separate constituent, at least one Helper Catalyst comprising an organic molecule, an organic ion or a mixture of organic molecules and organic ions, wherein a substance S is identifiable as a Helper Catalyst for an electrochemical reaction R that is catalyzed by a Catalytically Active Element M by applying a test comprising:

filling a three-electrode electrochemical cell with an electrolyte E suitable for effectuating reaction R, said electrochemical cell comprising a working electrode, a counter electrode and a reference electrode;

electrically connecting said Catalytically Active Element M to said working electrode and electrically connecting said working electrode to said counter electrode and to a source of electrical energy, thereby forming an electrical circuit;

employing said reference electrode to measure a reversible hydrogen electrode (RHE) potential in said electrolyte E;

loading at least one reactant for reaction R into said cell;

measuring a cyclic voltammogram for reaction R to identify a potential of a peak associated with reaction R;

calculating a difference V1 between RHE and an onset potential of said peak associated with reaction R;

calculating a difference V1A between RHE and a maximum potential of said peak associated with reaction R;

adding to said electrolyte E between 0.0001% and 99.9999% by weight of said Helper Catalyst;

measuring an RHE potential in electrolyte E with said added Helper Catalyst;

measuring a cyclic voltammogram of reaction R with said added Helper Catalyst;

calculating a difference V2 between RHE and an onset potential of said peak associated with reaction R;

calculating a difference V2A between RHE and a maximum potential of said peak associated with reaction R;

determining whether V2<V1 or V2A<V1A at any concentration of said Helper Catalyst between 0.0001% and 99.9999%; and identifying substance S as said Helper Catalyst for reaction R at concentrations when V2<V1 or V2A<V1A.

2. The electrocatalyst mixture of claim 1 wherein said electrocatalyst mixture, when electrical energy is applied, is capable of electrochemically converting $CO_2$ to at least one reaction product of reaction R with an overpotential decrease [V1-V2] of at least 0.5 V.

3. The electrocatalyst mixture of claim 2 wherein said at least one reaction product comprises at least one of CO, $HCO^-$, $(HCO_2)^-$, $H_2CO_2$, $CH_4$, $C_2H_4$, $CH_3CH_2OH$, $CH_3COO^-$, $CH_3COOH$, $C_2H_6$, $(COOH)_2$ and $(COO^-)_2$.

4. The electrocatalyst mixture of claim 3 wherein said at least one reaction product comprises at least one of $(HCO_2)^-$, $H_2CO_2$ and CO.

5. The electrocatalyst mixture of claim 3 wherein said Catalytically Active Element comprises at least one of Pt, Pd, Au, Ag, Ni, Fe, Co, Ru and Rh.

6. The electrocatalyst mixture of claim 1 wherein said Catalytically Active Element comprises at least one of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sm, Tb, La, Ce and Nd.

7. The electrocatalyst mixture of claim 1 wherein said Helper Catalyst comprises an organic cation selected from the group consisting of imidazoliums, pyridiniums, propulisoquinoliniums and thiuroniums of the formula:

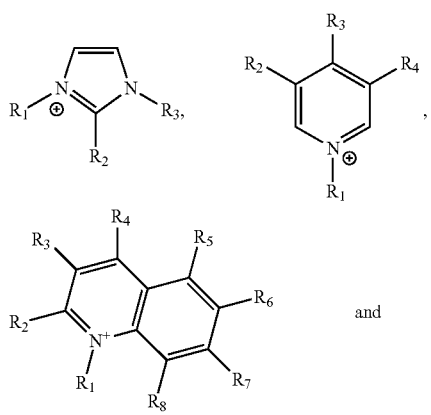

and

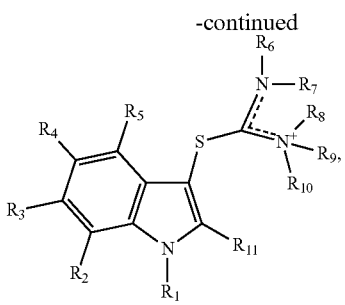

respectively, wherein for imidazoliums, $R_1$ and $R_3$ are independently selected from the group consisting of OH and any ligand containing at least one carbon atom, and $R_2$ is selected from the group consisting of H, OH and a ligand containing at least one carbon atom, and wherein for pyridiniums, propulisoquinoliniums, and thiuroniums, $R_1$ is selected from the group consisting of OH and a ligand containing at least one carbon atom, and $R_2$-$R_{11}$ are independently selected from the group consisting of H, OH and a ligand containing at least one carbon atom.

8. The electrocatalyst mixture of claim 1 wherein said Helper Catalyst has a concentration of between about 0.0000062% and 99.999% by weight.

9. The electrocatalyst mixture of claim 1 wherein said Helper Catalyst comprises at least one of a phosphine, an imidazolium having no nitrogen atom bonded to a hydrogen atom in an aromatic ring, a pyridinium having no nitrogen atom bonded to a hydrogen atom in an aromatic ring, a pyrrolidinium, a phosphonium, a sulfonium, a prolinate, and a methioninate.

10. The electrocatalyst mixture of claim 1 wherein said Helper Catalyst comprises a choline.

11. The electrocatalyst mixture of claim 1 wherein said Helper Catalyst comprises 1-ethyl-3-methylimidazolium cations.

12. The electrocatalyst mixture of claim 1 wherein said Helper Catalyst comprises tetrafluoroborate anions.

13. The electrocatalyst mixture of claim 1 wherein said Helper Catalyst is a solvent, an electrolyte or an additive.

14. A $CO_2$ sensor comprising the electrocatalyst mixture of claim 1.

15. A fuel cell comprising the electrocatalyst mixture of claim 1.

16. The electrocatalyst mixture of claim 1 wherein the Helper Catalyst does not comprise a Catalytically Active Element.

17. The electrocatalyst mixture of claim 1 wherein the Catalytically Active Element comprises at least a portion of an electrode selected from one of the anode and the cathode of an electrochemical cell.

18. The electrocatalyst mixture of claim 1 wherein the Catalytically Active Element comprises at least a portion of the cathode of an electrochemical cell.

19. An electrochemical device comprising the electrocatalyst mixture of claim 1, the Catalytically Active Element comprising at least a portion of an electrode, wherein the at least one Catalytically Active Element is selected from the group consisting of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sm, Tb, La, Ce and Nd.

20. The electrochemical device of claim 19 wherein the electrode is a cathode.

21. The electrochemical device of claim 19 wherein said Helper Catalyst comprises at least one of an organic cation and an organic anion.

22. The electrochemical device of claim 19 wherein said Helper Catalyst is selected from the group consisting of phosphines, imidazoliums having no nitrogen atom bonded to a hydrogen atom in an aromatic ring, pyridiniums having no nitrogen atom bonded to a hydrogen atom in an aromatic ring, pyrrolidiniums, phosphoniums, sulfoniums, prolinates, methioninates, cholines, choline chloride, choline bromide, and choline iodide.

23. The electrochemical device of claim 19 wherein said electrocatalyst mixture electrochemically converts $CO_2$ to at least one reaction product.

24. The electrochemical device of claim 23 wherein said electrocatalyst mixture electrochemically converts $CO_2$ to at least one reaction product comprising at least one of CO, $HCO^-$, $(HCO_2)^-$, $H_2CO_2$, $CH_4$, $C_2H_4$, $CH_3CH_2OH$, $CH_3COO^-$, $CH_3COOH$, $C_2H_6$, $(COOH)_2$ and $(COO^-)_2$.

25. The electrochemical device of claim 19 wherein said Helper Catalyst comprises a choline.

26. The electrochemical device of claim 19 wherein said Helper Catalyst is a solvent, an electrolyte or an additive.

27. The electrochemical device of claim 19 wherein the electrochemical device is a $CO_2$ sensor.

28. The electrochemical device of claim 19 wherein the electrochemical device is a fuel cell.

29. The electrochemical device of claim 19 wherein the electrode is a cathode.

30. A process for making a chemical reaction product, comprising the steps of:
   combining the Catalytically Active Element and the Helper Catalyst of claim 1 in the presence of a reactant; and
   allowing a reaction to proceed to produce a reaction product.

31. The process of claim 30 further comprising the step of:
   applying electrical energy to the reaction so as to achieve electrochemical conversion of the reactant to a reaction product.

32. The process of claim 30 wherein said Catalytically Active Element is selected from the group consisting of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sm, Tb, La, Ce and Nd.

33. The process of claim 32 wherein said Catalytically Active Element is selected from the group consisting of Pb, Hg, Tl, In, Cd, Bi, Zr, Cr, Sn, W, Pd and Ru.

34. The process of claim 30 wherein said Helper Catalyst comprises at least one of an organic cation and an organic anion.

35. The process of claim 30 wherein said Helper Catalyst is selected from the group consisting of phosphines, imidazoliums having no nitrogen atom bonded to a hydrogen atom in an aromatic ring, pyridiniums having no nitrogen atom bonded to a hydrogen atom in an aromatic ring, pyrrolidiniums, phosphoniums, sulfoniums, prolinates, methioninates, cholines, choline chloride, choline bromide, and choline iodide.

36. The process of claim 30 wherein said process is not photoelectrochemical.

37. The process of claim 30 wherein said reaction product is at least one of CO, $HCO^-$, $(HCO_2)^-$, $H_2CO_2$, $CH_4$, $C_2H_4$, $CH_3CH_2OH$, $CH_3COO^-$, $CH_3COOH$, $C_2H_6$, $(COOH)_2$, or $(COO^-)_2$.

38. The process of claim 37 wherein said reaction product is at least one of formic acid ($H_2CO_2$), formate ion ($(HCO_2)^-$) and carbon monoxide (CO).

39. The process of claim 30 wherein the Helper Catalyst does not comprise a Catalytically Active Element.

40. The process of claim 30 wherein the Catalytically Active Element comprises at least a portion of an electrode selected from one of the anode and the cathode of an electrochemical cell.

41. The process of claim 30 wherein the Catalytically Active Element comprises at least a portion of the cathode of an electrochemical cell.

42. The process of claim 30, wherein said reactant is carbon dioxide.

43. An electrochemical process for making a chemical reaction product, comprising the steps of:
providing at least one electrode comprising at least one Catalytically Active Element selected from the group consisting of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, C, In, Tl, Pb, Bi, Sb, Te, U, Sm, Tb, La, Ce and Nd;
combining the Catalytically Active Element and a separate Helper Catalyst in the presence of a reactant, the Helper Catalyst comprising an organic molecule, an organic ion, or a mixture of organic molecules and organic ions; and
applying electrical energy to the at least one electrode in order to carry out a reaction R so as to achieve electrochemical conversion of the reactant to a reaction product,
wherein reaction R is effectuated non-photoelectrochemically; and
wherein a substance S is identifiable as a Helper Catalyst for an electrochemical reaction R that is catalyzed by a Catalytically Active Element M by applying a test comprising:
filling a three-electrode electrochemical cell with an electrolyte E suitable for effectuating reaction R, said electrochemical cell comprising a working electrode, a counter electrode and a reference electrode;
electrically connecting said Catalytically Active Element M to said working electrode and electrically connecting said working electrode to said counter electrode and to a source of electrical energy, thereby forming an electrical circuit;
employing said reference electrode to measure a reversible hydrogen electrode (RHE) potential in said electrolyte E;
loading at least one reactant for reaction R into said cell;
measuring a cyclic voltammogram for reaction R to identify a potential of a peak associated with reaction R;
calculating a difference V1 between RHE and an onset potential of said peak associated with reaction R;
calculating a difference V1A between RHE and a maximum potential of said peak associated with reaction R;
adding to said electrolyte E between 0.0001% and 99.9999% by weight of said Helper Catalyst;
measuring an RHE potential in electrolyte E with said added Helper Catalyst;
measuring a cyclic voltammogram of reaction R with said added Helper Catalyst;
calculating a difference V2 between RHE and an onset potential of said peak associated with reaction R;
calculating a difference V2A between RHE and a maximum potential of said peak associated with reaction R;
determining whether V2<V1 or V2A<V1A at any concentration of said Helper Catalyst between 0.0001% and 99.9999%; and
identifying substance S as said Helper Catalyst for reaction R at concentrations when V2<V1 or V2A<V1A.

44. The process of claim 43 wherein said Helper Catalyst comprises at least one of an organic cation and an organic anion.

45. The process of claim 43 wherein said Helper Catalyst is selected from the group consisting of phosphines, imidazoliums having no nitrogen atom bonded to a hydrogen atom in an aromatic ring, pyridiniums having no nitrogen atom bonded to a hydrogen atom in an aromatic ring, pyrrolidiniums, phosphoniums, sulfoniums, prolinates, methioninates, cholines, choline chloride, choline bromide, and choline iodide.

46. The process of claim 43 wherein said reactant is $CO_2$.

47. The process of claim 43 wherein the reaction product is at least one of CO, $OH^-$, $HCO^-$, $(HCO_2)^-$, $H_2CO_2$, $CH_4$, $C_2H_4$, $CH_3CH_2OH$, $CH_3COO^-$, $CH_3COOH$, $C_2H_6$, $O_2$, $H_2$, $(COOH)_2$, $(COO^-)_2$, $Cl_2$, $Br_2$, $I_2$, NaOH, KOH, NaClO, $NaClO_3$, $KClO_3$, and $CF_3COOH$.

48. The process of claim 43 wherein said reaction product is at least one of formic acid ($H_2CO_2$), formate ion (($HCO_2$)$^-$) and carbon monoxide (CO).

49. An electrochemical device comprising:
an anode and a cathode, the cathode having a cathode potential and comprising at least one Catalytically Active Element, the cathode contacting a catholyte comprising a Helper Catalyst and carbon dioxide ($CO_2$), the Helper Catalyst comprising at least one of a phosphine, an imidazolium, a pyridinium, a pyrrolidinium, a phosphonium, a sulfonium, a prolinate, a methioninate, a choline, choline chloride, choline bromide and choline iodide;
wherein, when the Helper Catalyst comprises a five-member or a six-member aromatic ring, all ring nitrogen atoms are attached only to non-hydrogen atoms;
wherein, when electrical energy is applied to create a potential difference between the anode and the cathode, the electrochemical device is capable of converting at least a portion of the $CO_2$ to a predominant carbonaceous product when the cathode potential is equal to or more positive than −0.9 V versus the Standard Hydrogen Electrode (SHE), the conversion effectuated non-photoelectrochemically; and
wherein the predominant carbonaceous product consists of one of CO, $HCO^-$, $H_2CO$, $(HCO_2)^-$, $H_2CO_2$, $CH_4$, $C_2H_4$, $CH_3CH_2OH$, $CH_3COO^-$, $CH_3COOH$, $C_2H_6$, $(COOH)_2$ and $(COO^-)_2$.

50. The electrochemical device of claim 49, wherein the predominant carbonaceous product consists of one of carbon monoxide (CO,), formic acid ($H_2CO_2$,) and formate ions (($HCO_2$)$^-$).

51. The electrochemical device of claim 49, wherein a substance S is identifiable as a Helper Catalyst for an electrochemical reaction R that is catalyzed by a Catalytically Active Element M by applying a test comprising:
filling a three-electrode electrochemical cell with an electrolyte E suitable for effectuating reaction R, said electrochemical cell comprising a working electrode, a counter electrode and a reference electrode;
electrically connecting said Catalytically Active Element M to said working electrode and electrically connecting said working electrode to said counter electrode and to a source of electrical energy, thereby forming an electrical circuit;

employing said reference electrode to measure a reversible hydrogen electrode (RHE) potential in said electrolyte E;

loading at least one reactant for reaction R into said cell;

measuring a cyclic voltammogram for reaction R to identify a potential of a peak associated with reaction R;

calculating a difference V1 between RHE and an onset potential of said peak associated with reaction R;

calculating a difference V1A between RHE and a maximum potential of said peak associated with reaction R;

adding to said electrolyte E between 0.0001% and 99.9999% by weight of said Helper Catalyst;

measuring an RHE potential in electrolyte E with said added Helper Catalyst;

measuring a cyclic voltammogram of reaction R with said added Helper Catalyst;

calculating a difference V2 between RHE and an onset potential of said peak associated with reaction R;

calculating a difference V2A between RHE and a maximum potential of said peak associated with reaction R;

determining whether V2<V1 or V2A<V1A at any concentration of said Helper Catalyst between 0.0001% and 99.9999%; and identifying substance S as said Helper Catalyst for reaction R at concentrations when V2<V1 or V2A<V1A.

52. The electrochemical device of claim 51, wherein the addition of the Helper Catalyst for reaction R results in an overpotential reduction, defined as V1-V2, of at least 0.5 V.

53. The electrochemical device of claim 49, wherein the Catalytically Active Element is selected from the group consisting of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, C, In, Tl, Pb, Bi, Sb, Te, U, Sm, Tb, La, Ce and Nd.

54. The electrochemical device of claim 53, wherein the Catalytically Active Element comprises at least one of Ag, Au, Zn, Cd, Pd, Ga and Ni.

55. The electrochemical device of claim 53, wherein the Helper Catalyst comprises one of a choline and an imidazolium.

56. The electrochemical device of claim 49, wherein the predominant carbonaceous product is carbon monoxide (CO) and at least a portion of the $CO_2$ is convertible to CO when the cathode potential is equal to or less negative than −0.75 V versus the Standard Hydrogen Electrode (SHE).

57. The electrochemical device of claim 49, wherein the predominant carbonaceous product is formic acid ($H_2CO_2$) or formate ions (($HCO_2)^-$), and wherein the Helper Catalyst comprises a choline or an imidazolium.

58. The electrochemical device of claim 49, wherein the electrochemical device is capable of converting at least a portion of the $CO_2$ to the predominant carbonaceous product when the cathode potential is equal to or less negative than −0.75 V versus the Standard Hydrogen Electrode (SHE).

59. The electrochemical device of claim 49, wherein at least a portion of the $CO_2$ is convertible to the predominant carbonaceous product when the cathode potential is equal to or less negative than −0.6 V versus the Standard Hydrogen Electrode (SHE).

60. The electrochemical device of claim 49, wherein at least a portion of the $CO_2$ is convertible to the predominant carbonaceous product when the cathode potential is equal to or less negative than −0.4 V versus the Standard Hydrogen Electrode (SHE).

61. The electrochemical device of claim 49 comprising a $CO_2$ sensor or a fuel cell.

62. The electrochemical device of claim 49, comprising a cathode in contact with a catholyte, the catholyte having a pH, wherein the Helper Catalyst comprises organic cations, the Helper Catalyst serving as an electrolyte capable of supporting electrical current in the catholyte, whereby the electrochemical device is capable of operating at a current without addition of inorganic cations to the catholyte, with the proviso that a concentration of $H^+$ ions corresponding to the pH of the catholyte is present in the catholyte.

* * * * *